US011807892B2

(12) United States Patent
Goel

(10) Patent No.: US 11,807,892 B2
(45) Date of Patent: Nov. 7, 2023

(54) SINGLE-MOLECULE PLATFORM FOR DRUG DISCOVERY: METHODS AND APPARATUSES FOR DRUG DISCOVERY, INCLUDING DISCOVERY OF ANTICANCER AND ANTIVIRAL AGENTS

(71) Applicant: Nanobiosym, Inc., Cambridge, MA (US)

(72) Inventor: Anita Goel, Boston, MA (US)

(73) Assignee: Nanobiosym, Inc., Cambridge, MA (US)

( * ) Notice: Subject to any disclaimer, the term of this patent is extended or adjusted under 35 U.S.C. 154(b) by 0 days.

(21) Appl. No.: 16/850,895

(22) Filed: Apr. 16, 2020

(65) Prior Publication Data

US 2020/0308618 A1     Oct. 1, 2020

Related U.S. Application Data

(63) Continuation of application No. 15/860,205, filed on Jan. 2, 2018, now abandoned, which is a continuation
(Continued)

(51) Int. Cl.
*C12Q 1/00* (2006.01)
*C12Q 1/48* (2006.01)

(52) U.S. Cl.
CPC ............ *C12Q 1/00* (2013.01); *C12Q 1/48* (2013.01); *G01N 2333/16* (2013.01); *G01N 2333/91245* (2013.01); *G01N 2500/02* (2013.01)

(58) Field of Classification Search
CPC ......... B01L 3/502784; B01L 3/502761; B01L 3/502746; B01L 7/52; B01L 2200/10;
(Continued)

(56) References Cited

U.S. PATENT DOCUMENTS

| 4,683,195 A | 7/1987 | Mullis et al. |
| 4,683,202 A | 7/1987 | Mullis |

(Continued)

FOREIGN PATENT DOCUMENTS

| CN | 101558302 | 10/2009 |
| CN | 101868721 | 10/2010 |

(Continued)

OTHER PUBLICATIONS

Abbondanzieri et al., "Direct observation of base-pair stepping by RNA polymerase," Nature, 2005, vol. 438, pp. 460-465 (doi:10.1038/nature04268), Nature Publishing Group.
(Continued)

*Primary Examiner* — Michael L Hobbs
(74) *Attorney, Agent, or Firm* — Fish & Richardson P.C.

(57) ABSTRACT

One aspect of the invention provides a system for drug discovery, drug development, drug screening, or drug validation. The system includes: a sample chamber comprising a target protein and a drug candidate that may interfere with the target protein in the sample chamber, wherein the sample chamber is configured to: detect one or more of the following: (a) interference between the drug candidate the target protein and/or (b) one or more dynamics of the drug candidate on the target protein, wherein the one or more dynamics comprise affinity of the drug candidate to the target protein, and select the drug candidate if one or more desirable dynamics is detected. The system includes one or more immobilized surfaces and is configured to detect interactions between the drug candidate and the target protein at the single-molecule level.

20 Claims, 11 Drawing Sheets

Related U.S. Application Data of application No. 11/790,071, filed on Apr. 23, 2007, now Pat. No. 9,862,984.

(60) Provisional application No. 60/793,720, filed on Apr. 21, 2006.

(58) Field of Classification Search
CPC ..... B01L 2200/0647; B01L 2200/0673; B01L 2300/0883; B01L 2300/0867; B01L 2400/0487; B01L 2400/0545; B01L 2400/0448; B01L 2400/0424; B01F 3/0861; B01F 5/0646; B01F 5/0647; B01F 5/0403; B01F 13/0071; B01F 2215/0037; B01J 19/0046; B01J 19/0093; B01J 2219/0059; B01J 2219/0074; B01J 2219/0867; B01J 2219/00977; B01J 2219/00975; B01J 2219/00891; B01J 2219/00889; B01J 2219/00869; B01J 2219/0086; B01J 2219/00837; B01J 2219/00783; B01J 2219/00576; B01J 2219/00736; B01J 2219/00725; B01J 2219/00722; B01J 2219/00599; B01J 2219/00585; B01J 2219/00286; B82Y 30/00; C12Q 1/44; C12P 19/34; G01N 35/085; G01N 35/08; G01N 15/1484; Y02A 90/26; Y10T 436/2575; Y10T 436/118339
See application file for complete search history.

(56) References Cited

U.S. PATENT DOCUMENTS

| | | | |
|---|---|---|---|
| 4,965,188 | A | 10/1990 | Mullis et al. |
| 5,122,345 | A | 6/1992 | Tabor et al. |
| 5,413,906 | A | 5/1995 | Eberle et al. |
| 5,527,670 | A | 6/1996 | Stanley et al. |
| 5,545,540 | A | 8/1996 | Mian |
| 5,635,358 | A | 6/1997 | Wilding |
| 5,683,875 | A | 11/1997 | Lichtenwter |
| 5,753,439 | A | 5/1998 | Smith et al. |
| 5,824,477 | A | 10/1998 | Stanley |
| 5,856,174 | A | 1/1999 | Lipshutz et al. |
| 5,939,291 | A | 8/1999 | Loewy |
| 6,017,696 | A | 1/2000 | Heller |
| 6,033,850 | A | 3/2000 | Purvis |
| 6,174,670 | B1 | 1/2001 | Wittwer et al. |
| 6,197,508 | B1 | 3/2001 | Stanley |
| 6,214,587 | B1 | 4/2001 | Dattagupta et al. |
| 6,261,431 | B1 | 7/2001 | Mathies et al. |
| 6,277,605 | B1 | 8/2001 | Wijnhoven |
| 6,291,185 | B1 | 9/2001 | Purvis |
| 6,303,298 | B1 | 10/2001 | Gut et al. |
| 6,333,157 | B1 | 12/2001 | Miller-Jones |
| 6,344,326 | B1 | 2/2002 | Nelson et al. |
| 6,395,489 | B1 | 5/2002 | Stanley |
| 6,408,878 | B2 | 6/2002 | Unger et al. |
| 6,613,527 | B1 | 9/2003 | Stanley |
| 6,613,560 | B1 | 9/2003 | Tso et al. |
| 6,696,022 | B1 | 2/2004 | Chan et al. |
| 6,699,713 | B2 | 3/2004 | Milanovich et al. |
| 6,783,647 | B2 | 8/2004 | Culbertson et al. |
| 6,793,753 | B2 | 9/2004 | Unger et al. |
| 6,818,395 | B1 | 11/2004 | Quake et al. |
| 6,828,786 | B2 | 12/2004 | Scherer et al. |
| 6,911,345 | B2 | 6/2005 | Quake et al. |
| 6,929,030 | B2 | 9/2005 | Unger et al. |
| 6,960,437 | B2 | 11/2005 | Enzelberger et al. |
| 7,013,717 | B1 | 3/2006 | Struckmeier et al. |
| 7,033,764 | B2 | 4/2006 | Korlach et al. |
| 7,041,481 | B2 | 5/2006 | Anderson et al. |
| 7,169,556 | B2 | 1/2007 | Park et al. |
| 7,291,504 | B2 | 11/2007 | Seul |
| 7,315,376 | B2 | 1/2008 | Bickmore, Jr. et al. |
| 7,494,791 | B2 | 2/2009 | Goel |
| 8,632,973 | B2 | 1/2014 | Goel |
| 9,862,984 | B2 | 1/2018 | Goel |
| 2003/0027187 | A1 | 2/2003 | Strick et al. |
| 2004/0023207 | A1 | 2/2004 | Polansky |
| 2004/0096846 | A1 | 5/2004 | Seul |
| 2005/0170418 | A1* | 8/2005 | Moreland ......... B01L 3/502761 435/6.14 |
| 2006/0019274 | A1 | 1/2006 | Goel |
| 2007/0160175 | A1* | 7/2007 | Lang ..................... G02B 21/16 376/103 |
| 2007/0254279 | A1 | 11/2007 | Goel |
| 2008/0081329 | A1 | 4/2008 | Elliott et al. |
| 2008/0160630 | A1 | 7/2008 | Liu et al. |
| 2009/0148933 | A1 | 6/2009 | Battrell et al. |
| 2009/0246834 | A1 | 10/2009 | Goel |
| 2011/0005932 | A1 | 1/2011 | Jovanovich et al. |
| 2011/0059864 | A1* | 3/2011 | Farinas ................. C12Q 1/6872 435/287.1 |
| 2011/0244467 | A1 | 10/2011 | Haswell |
| 2011/0312622 | A1 | 12/2011 | Azimi et al. |
| 2012/0082985 | A1 | 4/2012 | Zenhausern et al. |
| 2014/0186940 | A1 | 7/2014 | Goel |
| 2014/0335527 | A1 | 11/2014 | Goel |
| 2016/0016171 | A1 | 1/2016 | Goel |

FOREIGN PATENT DOCUMENTS

| | | |
|---|---|---|
| CN | 102089079 | 6/2011 |
| CN | 102245305 | 11/2016 |
| EP | 1384022 | 1/2004 |
| EP | 1486785 | 12/2004 |
| JP | 2003507026 | 2/2003 |
| SG | 127211 | 6/2009 |
| WO | WO 1992/004470 | 3/1992 |
| WO | WO 1995/025177 | 9/1995 |
| WO | WO 1996/041864 | 12/1996 |
| WO | WO 1997/008293 | 3/1997 |
| WO | WO 1998/000562 | 1/1998 |
| WO | WO 1998/002573 | 1/1998 |
| WO | WO 1998/050147 | 11/1998 |
| WO | WO 1999/009042 | 2/1999 |
| WO | WO 1999/033559 | 7/1999 |
| WO | WO 2000/049176 | 8/2000 |
| WO | WO 2001/013088 | 2/2001 |
| WO | WO 2002/081729 | 10/2002 |
| WO | WO 2005/011867 | 2/2005 |
| WO | WO 2005/073691 | 8/2005 |
| WO | WO 2006/029387 | 3/2006 |
| WO | WO 2006/076022 | 7/2006 |
| WO | WO 2007/124105 | 11/2007 |
| WO | WO 2008/057781 | 5/2008 |
| WO | WO 2010/041088 | 4/2010 |
| WO | WO 2010/141139 | 12/2010 |
| WO | WO 2010/141921 | 12/2010 |
| WO | WO 2014/144548 | 9/2014 |

OTHER PUBLICATIONS

Andricioaei et al., "Dependence of DNA Polymerase Replication Rate on External Forces: A Model Based on Molecular Dynamics Simulations," Biophysical Journal, 2004, vol. 87, pp. 1478-1497, Biophysical Society.

Argaman et al., "Revealing the Mode of Action of DNA Topoisomerase I and its Inhibitors by Atomic Force Microscopy," Biochemical and Biophysical Research Communications, 301:789-797 (2003).

Australia Office Action for counterpart Australia Application No. 2009208132, Nano-PCR: Methods and Devices For Nucleic Acid Amplification And Detection, dated Sep. 12, 2012.

Australia Office Action, Australia Application No. 2005324505, dated Aug. 28, 2009.

Australia Office Action, Australia Application No. 2005324505, dated Dec. 24, 2009.

Australia Office Action, Australia Application No. 2005324505, dated Jul. 14, 2009.

(56) References Cited

OTHER PUBLICATIONS

Australia Office Action, Australia Application No. 2005324505, dated Nov. 19, 2007.
Australian Office Action, Australia Application No. 2005324505, dated May 18, 2009.
Australian Patent Office Communication Appl. No. 2009208132, dated Aug. 18, 2009.
Australian Patent Office Communication Appl. No. 2009208132, dated Sep. 2, 2009.
Babcock et al., "Relating the Microscopic and Macroscopic Response of a Polymeric Fluid in a Shearing Flow," Physical Review Letters, 2000, vol. 85, n. 9, pp. 2018-2021, The American Physical Society.
Bartley et al., "Exploration of the Transition State for Teriary Structure Formation between an RNA Helix and a Large Structured RNA," J. Mol. Biol., 328:1011-1026 Academic Press (2003).
Baumann et al., "Stretching of Single Collapsed DNA Molecules," Biophysical Journal, 2000, vol. 78, pp. 1965-1978, Biophysical Society.
Baumann, C.G., et al., "Ionic Effects on the Elasticity of Single DNA Molecules," Proc. Natl. Acad. Sci., USA, 94:6185-6190 (Jun. 1997).
Bennett, "A Brief History of Automatic Control", IEEE Control Systems, Jun. 1996, 17-25.
Berger et al., "Preparation and Properties of an Aqueous Ferrofluid", Journal of Chemical Education, 76(7): 943-948 (Jul. 1999).
Blanchard et al., "tRNA dynamics on the ribosome during translation," PNAS, 2004, vol. 101, n. 35, pp. 12893-12898, National Academy of Sciences.
Block et al., "Bead Movement by Single Kinesin Molecules Studied with Optical Tweezers," Nature, 348:348-352 (1990).
Bockelmann et al., "Unzipping DNA with Optical Tweezers: High Sequence Sensitivity and Force Flips," Biophysical Journal, 2002, vol. 82, pp. 1537-1553, Biophysical Society.
Bowen et al., "Single Molecule Studies of Synaptotagmin and Complexin Binding to the SNARE Complex," Biophys., vol. 89, pp. 690-702 (BioFAST, published on line Apr. 8, 2005, pp. 1-56 (with figures)), The Biophysical Society.
Braslavsky et al., "Sequence information can be obtained from single DNA molecules," PNAS, 2003, vol. 100, n. 7, pp. 3960-3964, National Academy of Sciences.
Brody et al., "Significance and statistical errors in the analysis of DNA microarray data," PNAS, 2002, vol. 99, n. 20, pp. 12975-12978, National Academy of Sciences.
Bryant et al., "Structural transitions and elasticity from torque measurements on DNA," Nature, 2003, vol. 424, pp. 338-106, Nature Publishing Group.
Burger et al., "IR Thermocycler for Centrifugal Microfluidic Platform with Direct On-Disk Wireless Temperature Measurement System", IEEE, 2011, 2867-2870.A270.
Bustamante et al., "Single-molecule studies of DNA mechanics,:" Current Opinion in Structural Biolmrv, 2000, vol. 10, pp. 279-285, Elsevier Science Ltd.
Bustamante et al., "Ten years of tension: single-molecule DNA mechanics," Nature, 2003, vol. 421, pp. 423-427, Nature Publishing Group.
Bustamante et al., "The Physics of Molecular Motors," Acc. Chem. Res., 2001, vol. 34, pp. 412-420, American Chemical Society.
Bustamante, "Of torques, forces, and protein machines," Protein Science, 2004, vol. 13, pp. 3061-3065, Cold Spring Harbor Laboratory Press.
Butler et al., "Brownian dynamics simulations of a flexible polymer chain which includes continuous resistance and multibody hydrodynamic interactions," The Journal of Chemical Physics, 2005, vol. 122, pp. 014901-1-014901-11, American Institute of Physics.
Caldarelli-Stefano et al., "Use of magnetic beads for tissue DNA extraction and IS6110 Mycobacterium tuberculosis PCR", J. Clin, Pathol: Mol. Pathol, 52: 158-163 (1999).
Charvin et al., "Single-molecule study of DNA unlinking by eukaryotic and prokaryotic type-II topoisomerases," PNAS, 2003, vol. 100, n. 17, National Academy of Sciences, pp. 9820-9825 (Aug. 19, 2003).

Charvin et al., "Tracking Topoisomerase Activity at the Single-Molecule Level," Annu. Rev. Biophys. Biomol. Struct., 2005, 34:203-219.
Chinese Office Action, Application No. 200580020306.2, dated Feb. 5, 2010.
Chou et al., "Disposable Microdevices for DNA Analysis and Cell Sorting," Proc. Solid-State Sensor and Actuator Workshop, Hilton Head, SC, Jun. 8-11, 1998, pp. 11-14.
Chou et al., "Integrated Elastomer Fluidic Lab-on-a-chip- Surface Patterning and DNA Diagnostics," Proceedings of Solid State Sensor and Actuator Workshop, Hilton Head, Jun. 2000, pp. 11-14.
Chou et al., "Microfabricated Devices for Sizing DNA and Sorting Cells," Micro- and Nanofabricated Structures and Devices for Biomedical Environmental Applications, Paul L. Gourley, Editor, Proceedings of SPIE, vol. 3258, pp. 181-187, 1998.
Chou et al., "A Microfabricated Rotary Pump," Biomedical Microdevices, 3(4):323-330, Kluwer Academic Publishers (2001).
Christen et al., "Localized closed-loop temperature control anhd regulation in hybrid silicon/silicone life science microsystems", IEEE, 2007, 2886-2889.
Cluzel et al., "DNA: An Extensible Molecule", Science, 271: 792-794 (Feb. 1996).
Davenport et al., "Single-Molecule Study of Transcriptional Pausing and Arrest by E. coli RNA Polymerase," Science, 2000, vol. 287, pp. 2497-2500, American Society for the Advancement of Science.
Dessinges et al., "Single-molecule assay reveals strand switching and enhanced processivity of UvrD," PNAS, 2004, vol. 101, n, 17, pp. 6439-6444, National Academy of Sciences.
Direction to Request Examination from Australian Patent Office, Australian Application No. 2009208132, dated Sep. 2, 2009.
Essevaz-Roulet et al., "Mechanical separation of the complementary strands of DNA," Proc. Natl. Acad. Sci. USA, 1997, vol. 94, pp. 11935-11940, The National Academy of Sciences.
European Office Action, EP Application No. 05856709.0, "Nano-PCR: Methods and Devices for Nucleic Acid Amplification and Detection" dated Jul. 2, 2009. (4272.1000-009).
European Patent Office Communication Appl. No. 07775933.0. 2404/2016415, dated Feb. 22, 2010.
European Patent Office Communication, Application No. 07775933. 0.2404/2016415, dated Dec. 3, 2009.
European Search Report for European Patent Application No. 05856709.0, "Nano-PCR: Methods and Devices for Nucleic Acid Amplification and Detection" dated May 23, 2008. (4272.1000-009).
Eyal et al., "Velocity-independent microfluidic flow cytometry," Electrophoresis, 2002, vol. 23, pp. 2653-2657, Wiley-VCR Verlag GmbH.
Fang et al., Microfluidic Analysis Chip, Zhaolun, pp. 123-125, Science Press, Mar. 2003.
Filing Receipt for Complete Application from Australian Patent Office, Application No. 2009208132, dated Aug. 18, 2009.
Filippova et al., "Quantifying Double-Strand Breaks and Clustered Damages in DNA by Single-Molecule Laser Fluorescence Sizing," Biophysical Journal, 2003, vol. 84, pp. 1281-1290, Biophysical Society.
Final Office Action for U.S. Appl. No. 11/790,071, "Single Molecule Platform For Drug Discovery: Methods And Apparatuses For Drug Discovery, Including Discovery Of Anticancer And Antiviral Agents", dated Jan. 23, 2017.
Final Office Action for U.S. Appl. No. 11/790,071, "Single Molecule Platform For Drug Discovery: Methods And Apparatuses For Drug Discovery, Including Discovery Of Anticancer And Antiviral Agents", dated Mar. 3, 2016.
Final Office Action for U.S. Appl. No. 12/321,825, "Nano-PCR: Methods and Devices for Nucleic Acid Amplification and Detection", dated Jun. 14, 2011.
Final Office Action for U.S. Appl. No. 14/106,399, "Nano-PCR: Methods And Devices For Nucleic Acid Amplification And Detection", dated Aug. 19, 2016.
Final Office Action for U.S. Appl. No. 14/202,791, "Systems And Methods For Mobile Device Analysis Of Nucleic Acids And Proteins", dated Mar. 23, 2017.

(56) References Cited

OTHER PUBLICATIONS

First Examination Report, India Application No. 9466/DELNP/2008, dated Jan. 16, 2013 (4272.1001-007).
Forde et al., "Using mechanical force to probe the mechanism of pausing and arrest during continuous elongation by *Escherichia coli* RNA polymerase," PNAS, vol. 99, n. 18, pp. 11682-11687, National Academy of Sciences. (Sep. 3, 2002).
Frothingham, "Applications of the Polymerase Chain Reaction to Infectious Disease Diagnosis," Annals of Saudi Medicine, 1996, vol. 16, pp. 657-665.
Fu et al., "A microfabricated fluorescence-activated cell sorter," Nature Biotechnology, 1999, vol. 17, pp. 1109-1111, Nature America Inc.
Fu et al., "An Integrated Microfabricated Cell Sorter," Anal. Chem., 2002, vol. 74, pp. 2451-2457, American Chemical Society.
Gai et al., "Visualizing Chemical Interactions in Life Sciences with Wide-Field Fluorescence Microscopy Towards the Single-Molecule Level," Trends in Analytical Chemistry, 26:980-992 (2007).
Gerton et al., "Tip-Enhanced Fluorescence Microscopy at 10 Nanometer Resolution," Physical Review Letters, 2004, vol. 93, n. 18, pp. 180801-1-4, The American Physical Society, pp. 180801-1-180801-4 (Oct. 29, 2004).
Goel et al., "Tuning and switching a DNA polymerase motor with mechanical tension," PNAS, 2003, vol. 100, n. 17, pp. 9699-9704, National Academy of Sciences.
Goel et al., "Tuning DNA "strings": Modulating the rate of DNA replication with mechanical tension," PNAS, 2001, vol. 98, n. 15, pp. 8485-8489, National Academy of Sciences.
Goel et al., "Unifying Themes in DNA Replication: Reconciling Single Molecule Kinetic Studies with Structural Data on DNA Polymerases," Journal of Biomolecular Structure & Dynamics, 2002, vol. 19, n. 4, pp. 1-14, Adenine Press.
Goel et al., "Harnessing Biological Motors To Engineer Systems For Nanoscale Transport And Assembly", Nature Nanotechnology, 1-11 (Jul. 2008).
Gore et al., "Bias and error in estimates of equilibrium free-energy differences from nonequilibrium measurements," PNAS, 2003, vol. 100, n. 22, National Academy of Sciences. (Oct. 28, 2003).
Ha et al., "Ligand-Induced Conformational Changes Observed in Single RNA Molecules," Proc. Natl. Acad. Sci. USA, 96:9077-9082 (1999).
Hansen et al., "A robust and scalable microfluidic metering method that allows protein crystal growth by free interface diffusion," PNAS, 2002, vol. 99, n. 26, National Academy of Sciences, pp. 16531-16536 (Dec. 24, 2002).
Hansen et al., "Microfluidics in structural biology: smaller, faster . . . better," Current Opinion in Structural Biology, 2003, vol. 13, pp. 538-544, Elsevier.
Hansen et al., "Systematic investigation of protein phase behavior with a microfluidic formulator," PNAS, 2004, vol. 101, n. 40, pp. 14431-14436, National Academy of Sciences.
Harada et al., "Single-Molecule Imaging of RNA Polymerase-DNA Interactions in Real Time," Biophysical Journal, 76:709-715 (1999).
Hong et al., "A nanoliter-scale nucleic acid processor with parallel architecture," Nature Biology, 2004, vol. 22, n. 4, pp. 435-439, Nature Publishing Group.
Hong et al., "Integrated nanoliter systems," Nature Biology, 2003, vol. 21, n. 10, pp. 1179-1183, Nature Publishing Group.
Huang, "Microfluidic Devices for Genomic Analysis," A dissertation presented to the faculty of Princeton University in candidacy for the degree of Doctor of Philosophy, Oct. 2003, pp. 1-95.
Hur et al., "Dynamics of dilute and semidilute DNA solutions in the start-up of shear flow," J. Rheol., 2001, vol. 45, n. 2, DD. 421-450, The Society of Rheology, Inc.
Hur et al., "Dynamics and configurational fluctuations of single DNA molecules in linear mixed flows," Physical Review, 2002, vol. 66, pp. O1 1915-1-011915-4, The American Physical Society.
Illingworth, Control Systems 2003, Univ. of Leeds, School of Biochemistry and Molecular Biology, available at http://www.bmb.leeds.ac.uk/illingworth/control/, Feb. 21, 2003.

India Patent Office Communication Appl. No. 6655/DELNP/2006, dated Nov. 30, 2009.
International Preliminary Report on Patentability for International Application No. PCT/US2014/029008, "Systems and Methods for Mobile Device Analysis of Nucleic Acids and Proteins"; dated Sep. 15, 2015.
International Preliminary Report on Patentability for PCT/US2005/016638, "Nano-PCR: Methods and Devices for Nucleic Acid Amplification and Detection" dated Oct. 30, 2007.
International Preliminary Report on Patentability, PCT/US2007/009747, "Single-Molecule Platform for Drug Discovery: Methods and Apparatuses for Drug Discovery, Including Discovery of Anticancer and Antiviral Agents" dated Oct. 30, 2008.
International Search Report and Written Opinion for PCT/US2005/016638, dated Oct. 3, 2007.
International Search Report and Written Opinion of the International Searching Authority, PCT/US2007/009747, dated Sep. 17, 2008.
Invitation to Pay Additional Fees for PCT/US2005/016638, dated Jul. 26, 2007.
Israel Office Action dated Aug. 29, 2010 for Application No. 179006 (4272.1000-011).
Israel Office Action dated Feb. 4, 2010 for Application No. 179006 (4272.1000-011).
Israel Office Action dated Jan. 14, 2009 for Application No. 179006 (4272.1000-011).
Israel Office Action dated Jun. 7, 2009 for Application No. 179006 (4272.1000-011).
Johnson et al., "Early Steps of Supported Bilayer Formation Probed by Single Vesicle Fluorescence Assays," Biophysical Journal, 2002, vol. 83, pp. 3371-3379, Biophysical Society.
Kartalov et al., "Microfluidic device reads up to four consecutive base pairs in DNA sequencing-by-synthesis," Nucleic Acids Research, 2004, vol. 32, n. 9, pp. 2873-2879, Oxford University Press.
Keller et al., "Relating Single-Molecule Measurements to Thermodynamics," Biophysical Journal, 2003, vol. 84, pp. 733-738, Biophysical Society.
Kim et al., "Mg2+-dependent conformational change of RNA studied by fluorescence correlation and FRET on immobilized single molecules," PNAS, 2002, vol. 99, n. 7, pp. 4284-4289, National Academy of Sciences.
Kovarova et al., "New specificity and yield enhancer of polymerase chain reactions," Nucleic Acids Research, 2000, vol. 28, n. 13, pp, i-iv, Oxford University Press.
Kuo and Sheetz, "Force of Single Kinesin Molecules Measured with Optical Tweezers," Science, 260:232-234 (1993).
Ladoux et al., "Direct imaging of single-molecules: from dynamics of a single DNA chain to the study of complex DNA-protein interactions," Science Progress, 2001, vol. 84, n. 4, pp. 267-290.
Lai et al., "Microsatellite mutations during the polymerase chain reaction: mean field approximations and their applications," Journal of Theoretical Biology, 2003, vol. 224, pp. 127-137, Elsevier Ltd.,.
Lang et al., "Combined optical trapping and single-molecule fluorescence," Journal of Biology, 2003, vol. 2, n. 1, Article 6, 2003 (published online at jbiol.com/content/2/1/6). 4 pages.
Lang et al., "Simultaneous, coincident optical trapping and single-molecule fluorescence," Nature Methods, 2004, vol. 1, n. 2, DD. 1-7, Nature Publishing Group. (Nov. 2004).
Larson et al., "Brownian dynamics simulations of a DNA molecule in an extensional flow field," J. Rheol., 1999, vol. 42, n. 2, pp. 267-304, The Society of Rheology, Inc.
Larson, "Hydrodynamics of a DNA molecule in a flow field," Physical Review, 1997, vol. 55, n. 2, pp. 1794-1797, The American Physical Society.
Li et al., "DNA molecules and configurations in a solid-state nanopore microscope," Nature Materials, 2003, vol. 2, pp. 611-615, Nature Publishing Group.
Li et al., "Rapid spontaneous accessibility of nucleosomal DNA," Nature Structural & Molecular Biology, 2005, vol. 12, n. 1, pp. 46-53, Nature Publishing Group.

(56) References Cited

OTHER PUBLICATIONS

Lia et al., "Supercoiling and denaturation in Gal repressor/heat unstable nucleoid protein (HU)-mediated DNA looping," PNAS, 2003, vol. 100, n. 20, National Academy of Sciences, pp. 11373-11377 (Sep. 30, 2003).
Liphardt et al., "Reversible Unfolding of Single RNA Molecules by Mechanical Force," Science, 2001, vol. 292, pp. 733-737, American Society for the Advancement of Science.
Liu et al., "A Low-Cost Microfluidic Chip for Rapid Genotyping of Malaria-Transmitting Mosquitoes", PLOS One, 7(8): 7 pgs. (Aug. 2012).
Liu et al., A nanoliter rotary device for polymerase chain reaction,: Electrophoresis, 2002, vol. 23, pp. 1531-1536, Wiley-VCR Verlag GmbH.
Liu et al., "Solving the "World-to-Chip" Interface Problem with a Microfluidic Matrix," Analytical Chemistiy, vol. 75, n. 18, pp. 4718-4723, American Chemical Society. (Aug. 16, 2003).
Maier et al., "Replication by a single DNA polymerase of a stretched single-stranded DNA," PNAS, 2000, vol. 97, n. 22, pp. 12002-12007, National Academy of Sciences.
Mann et al. "Control Systems and Homeostatis, In The Nervous System in Action, Chapter 2", Jul. 20, 2011, 7 pages, (www://michaeldmann.net/mann2.html.
Marko et al., "Twist and shout (and pull): Molecular chiropractors undo DNA," Proc. Natl. Acad. Sci. USA, 1997, vol. 94, pp. 11770-11772, The National Academy of Sciences.
Meiners et al., "Femtonewton Force Spectroscopy of Single Extended DNA Molecules," Physical Review Letters, 2000, vol. 84, n. 21, The American Physical Society, pp. 5014-5017 (May 22, 2000).
Michael et al., "Evaluation of Polymerase Chain Reaction for Rapid Diagnosis of Tuberculosis Meningitis," Indian Journal of Tuberculosis, 2002, vol. 49, pp. 133-137.
Miller et al., "Microfluidic device incorporating closed loop feedback control for uniform and tunable production of micro-droplets", Lab on a Chip, May 2010, 10: 1293-1301.
Mosadegh et al., "Next-generation integrated microfluidic circuits" Lab on a Chip, Sep. 2011, 11(17): 2813-2818.
Munce et al., "Single Cell Analysis on a Microchip Platform using Optical Tweezers and Optical Scissors," in Micromachining and Microfabrication 2003:, Microfluidics, BioMEMS, and Medical Microsystems, SPIE 4982, San Jose, CA, Jan. 27-29, 2003, pp. 28-36.
Munson et al., "Image-based feedback control for real-time sorting of microspheres in a microfluidic device", Lab on a Chip, 2010 Sep. 2010, 10: 2402-2410.
Namasivayam et al., "Light-Induced Molecular Cutting: Localized Reaction on a Single DNA Molecule," Analytical Chemistry, 2003, vol. 75, n. 16, pp. 4188-4194, American Chemical Society.
Namasivayam et al., "Electrostretching DNA molecules using poler-enhanced media within microfabricated devices", Analytical Chemistiy, 2002, 74(14): 3378-3385.
Neuman et al. "Single-Molecule force spectroscopy: optical tweezers, magnetic tweezers and atomic force Microscopy" Nat. Methods. Jun. 2008, 5(6): 491-505.
Neuman et al., "Optical trapping," Review of Scientific Instruments, 2004, vol. 75, n. 9, American Institute of Physics. DD. 2787-2808 (Sep. 2004).
Neuman et al., "Ubiquitous Transcriptional Pausing Is Independent of RNA Polymerase Backtracking," Cell, 2003, vol. 115, pp. 437-447, Cell Press.
New Zealand Examination Report Appl. No. 551996, dated Feb. 1, 2010.
New Zealand Office Action, New Zealand Application No. 551996, dated Jun. 20, 2008.
New Zealand Office Action, New Zealand Application No. 551996, dated Mar. 8, 2010.
New Zealand Office Action, New Zealand Application No. 551996, dated Sep. 15, 2009.
New Zealand Office Action, New Zealand Application No. 582558, dated Jan. 19, 2010.
Notice of Allowance for U.S. Appl. No. 11/790,071, "Single-Molecule Platform For Drug Discovery: Methods And Apparatuses For Drug Discovery, Including Discovery Of Anticancer And Antiviral Agents", dated Aug. 30, 2017.
Notification of Acceptance from Australian Patent Office, Application No. 2005324505, dated Aug. 28, 2009.
Notification of Grant from Singapore Patent Office, Singapore Application No. 200607685-5, dated Jun. 30, 2009.
Notification of Sealing from Australian Patent Office, Application No. 2005324505, dated Dec. 24, 2009.
Notification of Transmittal of the International Search Report and The Written Opinion of the International Searching Authority, or the Declaration for International Application No. PCT/US2014/029008, "Systems and Methods for Mobile Device Analysis of Nucleic Acids and Proteins"; dated Oct. 13, 2014.
Notomi et al., "Loop-mediated isothermal amplification of DNA", Nucleic Acids Research, 28(12): e63, 7 pgs (2000).
Office Action for U.S. Appl. No. 11/790,071, "Single Molecule Platform For Drug Discovery: Methods And Apparatuses For Drug Discovery, Including Discovery Of Anticancer And Antiviral Agents", dated Aug. 29, 2016.
Office Action for U.S. Appl. No. 14/106,399, "Nano-PCR: Methods And Devices For Nucleic Acid Amplification And Detection", dated Jan. 22, 2018 (4272.1000-027).
Office Action for U.S. Appl. No. 14/106,399, "Nano-PCR: Methods And Devices For Nucleic Acid Amplification And Detection", dated Mar. 28, 2017, (4272.1000-027).
Office Action for U.S. Appl. No. 14/202,791, "Systems And Methods For Mobile Device Analysis Of Nucleic Acids And Proteins", dated Sep. 9, 2016. (4272.1003-002).
Office Action for U.S. Appl. No. 14/777,194, "Systems And Methods For Mobile Device Analysis Of Nucleic Acids And Proteins", dated Sep. 25, 2017.
Perkins et al., "Direct Observation of Tube-Like Motion of a Single Polymer Chain," Science, 1994, vol. 264, pp. 819-822, American Society for the Advancement of Science.
Perkins et al., "Forward and Reverse Motion of Single RecBCD Molecules on DNA," Biophysical Journal, 2004, vol. 86, pp. 1640-1648, Biophysical Society.
Perkins et al., "Relaxation of a Single DNA Molecule Observed by Optical Microscopy," Science, 1994, vol. 264, pp. 822-826, American Society for the Advancement of Science.
Perkins et al., "Sequence-Dependent Pausing of Single Lambda Exonuclease Molecules," Science, 2003, vol. 301, pp. 1914-1918, American Society for the Advancement of Science.
Perkins et al., "Single Polymer Dynamics in an Elongational Flow," Science, 1997, vol. 276, pp. 2016-2021, American Society for the Advancement of Science.
Perkins et al., "Stretching of a Single Tethered Polymer in a Uniform Flow," Science, 1995, vol. 268, pp. 83-87, American Society for the Advancement of Science.
Pope et al., "Force-induced melting of a short DNA double helix," Eur. Biophys. J., 30: 53-62 (2001) (month of publication not available).
Prasad, "Introduction to Biophotonics", pp. 435-437, Zhejiang University Press 2006 (with English translation of Chinese Office Action for Application No. 201480021900.2, "Systems and Methods for Mobile Device Analysis of Nucleic Acids and Proteins", dated Mar. 23, 2017).
Prudnikov et al., "Chemical methods of DNA and RNA fluorescent labeling", Nucleic Acids Research, 1996, 24(220): 4535-4542.
Qiu et al., "A portable, integrated analyzer for microfluidic-based molecular analysis", Biomed Microdevices, vol. 13 (May 27, 2011), pp. 809-817.
Quake et al., "From Micro- to Nanofabrication with Soft Materials," Science, 2000, vol. 290, pp. 1536-1540, American Society for the Advancement of Science.
Quake et al., "The dynamics of partially extended single molecules of DNA," Nature, 1997, vol. 388, pp. 151-154, Nature Publishing Group.
Quint et al., "Reliability of Methods for Hepatitis B Virus DNA Detection," Journal of Clinical Microbiology, 1995, vol. 33, n. 1, pp. 225-228, American Society for Microbiology.

(56) References Cited

OTHER PUBLICATIONS

Reese et al., "Microfabricated Fountain Pens for High-Density DNA Arrays," Genome Research, 2003, vol. 13, pp. 2348-2352, Cold Spring Harbor Laboratory Press.
Rice et al., "Building and Using Optical Traps to Study Properties of Molecular Motors," Methods in Enzymology, 361:112-133 (2003).
Ritort et al., "A two-state kinetic model for the unfolding of single molecules by mechanical force," PNAS, 2002, vol. 99, n. 21, pp. 13544-13548, National Academy of Sciences.
Rolland et al., "Solvent-Resistant Photocurable "Liquid Teflon" for Microfluidic Device Fabrication," J. Am. Chem. Soc., 2004, vol. 126, pp. 2322-2323, American Chemical Society.
Ros et al., "Single molecule force spectroscopy on ligand-DNA complexes: from molecular binding mechanisms to biosensor application," Journal of Biotechnology, 2004, vol. 112, pp. 5-12, Elsevier.
Rosenfeld et al., "Stepping and Stretching," The Journal of Biological Chemistry, 2003, vol. 278, n. 20, pp. 18550-18556, JBC Papers in Press.
Rouzina, I. et al., "Force-Induced Melting of the DNA Double Helix," Biophysical Journal, 80:882-893 (2001).
Russell et al., "Exploring the folding landscape of a structured RNA," PNAS, 2002, vol. 99, n. 1, pp. 155-160, National Academy of Sciences.
Rusu et al., "Direct Integration of Micromachined Pipettes in a Flow Channel for Single DNA Molecule Study by Optical Tweezers," Journal of Microelectromechanical Systems, 2001, vol. 10, n. 2, pp. 238-245.
Schafer and Radmacher, "Influence of Myosin II Activity on Stiffness of Fibroblast Cells," Acta Biomaterialia, 1:273-280 (2005).
Scherer et al., Monolithic Integration of Microfluidics and Optoelectronics for Biological Analysis, ARO Grant No. DAAD 19-00-1-0392 DARPA Biofips Report on Standard Form 298, Apr. 15, 2004.
Schnitzer et al., "Force production by single kinesin motors," Nature Cell Biology, 2000, vol. 2, pp. 718-723, Macmillan Magazines, Ltd.
Schroeder et al., "Dynamics of DNA in the Flow-Gradient Plane of Steady Shear Flow: Observations and Simulations," Macromolecules, 2005, vol. 38, pp. 1967-1978, American Chemical Society.
Schroeder et al., "Effect of Hydrodynamic Interactions on DNA Dynamics in Extensional Flow: Simulation and Single Molecule Experiment," Macromolecules, 2004, vol. 37, pp. 9242-9256, American Chemical Society.
Search Report for China Application No. 201480021900.2, "Systems and Methods for Mobile Device Analysis of Nucleic Acids and Proteins", dated Aug. 17, 2016.
Search Report for China Application No. 201480021900.2, "Systems and Methods for Mobile Device Analysis of Nucleic Acids and Proteins", dated Mar. 9, 2017.
Search Report for Singapore Application No. 11201507590Q, "Systems and Methods for Mobile Device Analysis of Nucleic Acids and Proteins", dated Jun. 21, 2016. (4272,1003-014).
Shaevitz et al., "Backtracking by single RNA polymerase molecules observed at near-base-pair resolution," Nature, 2003, vol. 426, pp. 684-687, Nature Publishing Group.
Shivashankar et al., "RecA polymerization on double-stranded DNA by using single-molecule manipulation: The role of ATP hydrolysis," PNAS, 1999, vol. 96, pp. 7916-7921, National Academy of Sciences.
Singapore Notification of Grant Appl. No. 200607685-5, dated Jun. 30, 2009.
Singh-Zocchi et al., "Single-molecule detection of DNA hybridization," PNAS, 2003, vol. 100, n. 13, pp. 7606-7610, National Academy of Sciences.
Smith et al., "Dynamical Scaling of DNA Diffusion Coefficients," Macromolecules, 1996, vol. 29, pp. 1372-1373, American Chemical Society.
Smith et al., "Response of Flexible Polymers to a Sudden Elongational Flow," Science, 1998, vol. 281, pp. 1335-1340, American Society for the Advancement of Science.
Smith et al., "Self-Diffusion of an Entangled DNA Molecule by Reptation," Physical Review Letters, 1995, vol. 75, n. 2, The American Physical Society, pp. 4146-4149 (Nov. 27, 1995).
Smith et al., "Single-Polymer Dynamics in Steady Shear-Flow," Science, 1999, vol. 283, pp. 1724-1727, American Society for the Advancement of Science.
Smith et al., "The bacteriophage phi 29 portal motor can package DNA against a large internal force," Nature, 2001, vol. 413, pp. 748-752, Nature Publishing Group.
Smith et al., "Direct Mechanical Measurements of the Elasticity of Single DNA Molecules by Using Magnetic Beads," Science, 258:1122-1126 (1992).
Smith et al., "Overstretching B-DNA: The Elastic Response of Individual Double-Stranded and Single-Stranded DNA Molecules," Science, 271:795-799 (I 996).
Spies et al., "A Molecular Throttle: The Recombination Hotspot x Controls DNA Translocation by the RecBCD Helicase," Cell Press, 114:647-654 (2003).
Strick et al., "Micro-mechanical measurement of the torsional modulus of DNA," Genetica, 1999, vol. 106, pp. 57-62, Springer.
Strick et al., "Phase coexistence in a single DNA molecule," Physica A, 1999, v. 263, pp. 392-404, Elsevier Science.
Strick et al., "Twisting and Stretching Single DNA Molecules," Progress in Biophysics & Molecular Biology, 74:115-140 (2000).
Strunz et al., "Dynamic force spectroscopy of single DNA molecules," Proc. Natl. Acad. Sci. USA, 96: 11277-11282 (Sep. 1999).
Supplementary European Search Report for European Patent Application No. 05856709.0, dated May 23, 2008 (4272.1000-009).
Supplementary European Search Report, Application No. 07775933. 0.2404/2016415, dated Nov. 16, 2009.
Svoboda-Newman et al., "Detection of hepatitis C by RT-PCR in formalin-fixed paraffin-embedded tissue from liver transplant patients," Diagn. Mol. Pathol., 1997, vol. 6, n. 2, pp. 123-129 (Abstract from PubMed), National Library of Medicine.
Thorsen et al., "Dynamic Pattern Formation in a Vesicle-Generating Microfluidic Device," Physical Review Letters, 2001, vol. 86, n. 18, The American Physical Society, pp. 4163-4166 (Apr. 30, 2001).
Thorsen et al., "Microfluidic Large-Scale Integration," Science, 2002, vol. 298, pp. 580-584, American Society for the Advancement of Science.
Uhlendorf et al., "Long-term model predictive control of gene expression at the population and single-cell levels", PNAS, Aug. 28, 2012, 109(35): 14271-14276.
Van Dam et al., "Gene Expression Analysis with Universal n-mer Arrays," Genome Research, 2002, vol. 12, pp. 145-152, Cold Spring Harbor Laboratory Press.
Van Oijen et al., "Single-Molecule Kinetics of Exonuclease Reveal Base Dependence and Dynamic Disorder," Science, 2003, vol. 301, pp. 1235-1238.
Van Den Broek et al., "DNA-tension dependence of restriction enzyme activity reveals mechanochemical properties of the reaction pathway," Nucleic Acids Research, 2005, vol. 33, n. 8, pp. 2676-2684, Oxford University Press.
Vincent, "Helicase-dependent isothermal DNA amplification", EMBO Reports, 5(8): 795-800 (2004).
Voulgarakis et al., "Probing The Mechanical Unzipping Of DNA", PCAS, 87(15): 64-70 (Feb. 2008).
Voulgarakis et al., "Sequencing DNA by Dynamic Force Spectroscopy: Limitations and Prospects," Nano Letters, 6(7):1483-1486 (2006).
Walker et al., "Isothermal in vitro amplification of DNA by a restriction enzyme/DNA polymerase system," Proc. Natl. Acad. Sci USA, 89: 392-396 (Jan. 1992).
Wang et al., "Force and Velocity Measured for Single Molecules of RNA Polymerase," Science, 1998, vol. 282, pp. 902-907, American Association for the Advancement of Science.
Wang et al., "Stretching DNA with Optical Tweezers", Biophysical Journal, 72: 1335-1346 (Mar. 1997).
Wang, "Design and Manufacture of MicroSystems", First Edition, p. 603, Tsinghua University Press, 2008.
Wang, "Design Technique and Quality Assurance in AIDS Lab," p. 132, Science Press, Jan. 15, 2009 (with English translation of Chinese Office Action for Application No. 201480021900.

(56) References Cited

OTHER PUBLICATIONS

2,"Systems and Methods for Mobile Device Analysis of Nucleic Acids and Proteins", dated Mar. 23, 2017).

Washizu, M., et al., "Manipulation of DNA Molecules in Micro-Structures", DECHEMA Monographs, 1996, 132: 177-194.

Weninger et al., "Single-molecule studies of SNARE complex assembly reveal parallel and antiparallel configurations," PNAS, 2003, vol. 100, n. 25, pp. 14800-14805, National Academy of Sciences.

Wong et al., "Deformation of DNA molecules by hydrodynamic focusing," J. Fluid Mech., 2003, vol. 497, pp. 55-65, Cambridge University Press.

Wulte et al., "Single-molecule studies of the effect of template tension on T7 DNA polymerase activity," Nature, 404:103-106 (2000).

Yang et al., "Integrated Multi-Process Microfluidic Systems for Automating Analysis", JALA Charlottesv Va. Jun. 2010, 15(3): 198-209.

Yin et al., "Transcription Against an Applied Force," Science, 270:1653-1657 (1995).

Zhuang et al., "A Single-Molecule Study of RNA Catalysis and Folding," Science, 2000, vol. 288, pp. 2048-2051, American Society for the Advancement of Science.

Zhuang et al., "Correlating Structural Dynamics and Function in Single Ribozyme Molecules," Science, 2002, vol. 296, pp. 1473-1476, American Society for the Advancement of Science.

Zhuang et al., "Fluorescence quenching: A tool for single-molecule protein-folding study," PNAS, 2000, vol. 97, n. 26, pp. 14241-14244, National Academy of Sciences.

Zimmerman et al., "DNA stretching on functionalized gold surfaces," Nucleic Acids Research, 1994, vol. 22, n. 3, pp. 492-497, Oxford University Press.

\* cited by examiner

Quadrant detection system analyzes Brownian Motion of Bead in an optical trap to determine pN forces with high resolution.

FIG. 9

NANO-VALID™ System

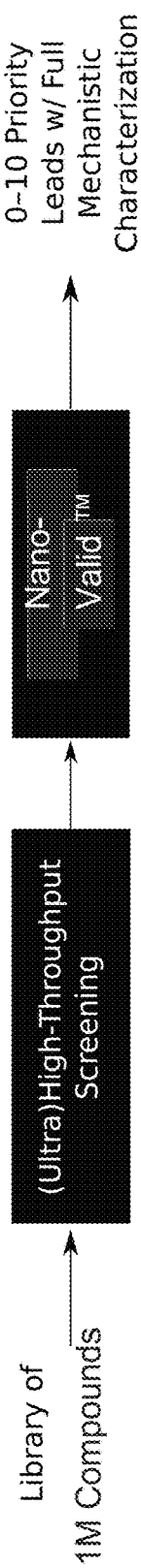

Library of 1M Compounds → (Ultra)High-Throughput Screening → Nano-Valid™ → 0-10 Priority Leads w/ Full Mechanistic Characterization

| | (Ultra) High-Throughput Screening | Nano-Valid™: ID Priority Leads with Mechanism Characterization |
|---|---|---|
| Time | 10 days (@100,000/day)–100 days (@10,000/day) | 3,000 minutes ~= 2 days (@ 3 minutes/lead) For 1,000 Lead Hits examined with single instrument |
| Implementation | Robotics or manual plate reading | Single manual Benchtop Instrument Assay could utilize existing HTS plates and fluidic delivery systems |
| Total Cost | Per Compound Cost Highly Variable Capital Cost Variable | Per Lead ~ Same Cost/Lead as HTS 48 hours of technician labor + reagents + supplies (e.g., plates) Capital Cost: $4 M/Instrument |
| Reagent Efficiency | Reagent Efficiency Ratio: 1 (96 well) 20,000 (ultra) | Reagent Efficiency Ratio: 20-200 (i.e., 1-10uL target/lead) |
| Quality of Answer | Inaccurate "Yes/No" Answer | Highly Accurate "Yes/No" answer. Precise characterization of inhibition mechanism |

FIG. 10

Nano-Valid Advantages

Nano-Valid approach simultaneously provides
- Highly accurate "Yes/No" answer for each lead
- Elimination of false artifactual leads from the HTS
- Detailed enzymatic dynamics data which precisely characterize the inhibition/interference mechanism Medium-throughput interrogation of hit leads (~3 minutes/lead)
- Future microfluidic/automated implementations could further improve this to high throughput (<<1 minute/lead) to make it competitive with HTS Highly Cost-effective
- Similar volumes to HTS
- Very Low capital costs, Low costs per assay (Comparable to HTS)

Nano-Valid prep could be integrated into existing HTS infrastructure (e.g., fluidics delivery, etc.)

SINGLE-MOLECULE PLATFORM FOR DRUG DISCOVERY: METHODS AND APPARATUSES FOR DRUG DISCOVERY, INCLUDING DISCOVERY OF ANTICANCER AND ANTIVIRAL AGENTS

RELATED APPLICATIONS

This application is a continuation of U.S. patent application Ser. No. 15/860,205, filed on Jan. 2, 2018, which is a continuation of U.S. patent application Ser. No. 11/790,071, filed on Apr. 23, 2007, now U.S. Pat. No. 9,862,984, which claims the benefit of U.S. Provisional Patent Application Ser. No. 60/793,720, filed on Apr. 21, 2006, the entire teachings of which are incorporated herein by reference.

FIELD OF THE INVENTION

The invention relates to the screening and validation of drug candidates that target enzymes, including DNA polymerases, RNA polymerases, and reverse-transcriptases.

BACKGROUND OF THE INVENTION

Approximately thirty percent of drugs in clinical use inhibit a disease-related enzymatic process (Copeland, R. A. Evaluation of enzyme inhibitors in drug discovery: a guide for medicinal chemists and pharmacologists. (Wiley-Interscience, 2005)). Thus, the discovery of new enzyme inhibitors is an important area of research in biochemistry and pharmacology.

Polymerase inhibitors are valuable in both clinical and research settings. These inhibitors help in elucidating the mechanistic aspects of transcription and DNA replication, in mapping structure-function relationships, and in characterizing protein activity. Polymerase inhibitors are also among the most attractive drug targets. Knowledge about these inhibitors, their structures, and their mechanisms enable the design of new drugs such as anti-cancer agents, antiviral agents, and antibiotics that will be effective against new pathogens and antibiotic resistant mutants of known pathogens. Because some of these inhibitors have been reported to induce and/or inhibit apoptosis, they also provide valuable tools for investigating apoptosis. Likewise, because some of these agents block specific steps of DNA transcription, polymerase inhibitors can help to elucidate the role of transcriptional control in regulating the expression of target genes in various healthy and disease states.

Drugs that target polymerase proteins involved in particular disease pathways are well known in the art. Reverse transcriptase inhibitors (RTIs), for example, are a class of antiretroviral drugs that target construction of viral DNA by inhibiting the activity of reverse transcriptase.

There are two subtypes of RTIs with different mechanisms of action: nucleoside and nucleotide analogue RTIs are incorporated into the viral DNA leading to chain termination, while non-nucleoside-analog RTIs act as competitive inhibitors of the reverse transcriptase enzyme. Current AIDS therapeutics that function by inhibiting HIV reverse transcriptase are described in the art (see, e.g., Bean et al., Appl Environ Microbiol 72:5670-5672 (2005)), and include Efavirenz (brand names SUSTIVA® and STOCRIN®) and Nevirapine (also marketed under the trade name VIRAMUNE®). Antibiotics that target polymerase proteins (e.g. rifampin) and cancer drugs that target polymerase proteins (e.g. cisplatin) are also known in the art.

Many drugs have been found to be efficacious in the treatment of cancer. These include diverse chemical compounds such as antimetabolites (e.g., methotrexate and fluorouracil), DNA-damaging agents (e.g., cyclophosphamide, cisplatin, and doxorubicin), mitotic inhibitors (e.g., vincristine), nucleotide analogues (e.g., 6-mercaptopurine), inhibitors of topoisomerases involved in DNA repair (e.g., etoposide), inhibitors of DNA polymerase (e.g., bleomycin), and intercalating agents like mitoxantrone.

Several drugs targeting enzymes of mammalian DNA replication are currently being investigated as promising candidates for cancer chemotherapy or as probes for understanding. the roles of specific enzymes in DNA replication and repair. These potential drug candidates include corylifolin, bakuchiol, resveratrol, Neobavaisoflavone, and daidzein (see Sun et al., J. Nat. Prod. 61, 362-366 (1998)).

Other examples of DNA and RNA polymerase inhibitors include Actinomycin D, *Streptomyces* sp.; a-Amanitin, *Amanita* sp.; Aphidicolin, HSY replication inhibitor, BPS; Methyl a-Amanitin Oleate; Novobiocin, Sodium Sait; Rifampicin; RNA Polymerase III Inhibitor; and Actinomycin D, 7-Amino. Three polymerase inhibitors currently in Phase II trials for use against Hepatitis C Virus are Idenix/Novartis' valopicitabine (NM283); ViroPharma's HCV-796; and Roche's R1 626. Roche/Idenix are also investigating valtorcitabine (val-LdC), a first strand viral DNA synthesis inhibitor in Phase II HCV trials after initial success as an HBV treatment.

DNA damaging agents provide some of the most successful treatments for cancer. The enzyme Poly(ADP-ribose) polymerase (i.e. PARP) can help repair DNA damage caused by the DNA damaging agents used to treat cancer. As PARP activity is often increased in cancer cells, it provides these cells with a survival mechanism. ABT-888 (Abbott Oncology), for example, is an oral PARP-inhibitor developed by Abbott to prevent DNA repair in cancer cells and increase the effectiveness of common cancer therapies such as radiation and alkylating agents. Moreover, preclinical data indicates ABT-888 has improved the effectiveness of radiation and many types of chemotherapy in animal models of cancer.

These selected publications from the last 5 years illustrate the current state of the artwith regard to the activity, mechanisms, and biochemistry of polymerase inhibitors:

Brown J A, Duym W W, Fowler J D, Suo, Z., (2007) "Single-turnover Kinetic Analysis of the Mutagenic Potential of 8-Oxo-7,8-dihydro-2'-deoxyguanosine during Gap-filling Synthesis Catalyzed by Human DNA Polymerases lambda and beta." J Mol Biol. [Epub ahead of print]

Suo, Z., Abdullah M A. (2007) "Unique Composite Active Site of the Hepatitis C Virus NS2-3 Protease: a New Opportunity for Antiviral Drug Design." ChemMedChem. 2(3), 283-284.

Roettger M P, Fiala K A, Sompalli S, Dong Y, Suo Z. (2004) "Pre-steady-state kinetic studies of the fidelity of human DNA polymerase mu", Biochemistry 43(43), 13827-38.

Fiala K A, Abdel-Gawad W, Suo Z. (2004) "Pre-steady-state kinetic studies of the fidelity and mechanism of polymerization catalyzed by truncated human DNA polymerase lambda.", Biochemistry 43(21), 6751-62.

Fiala, K. A & Suo Z.* (2004) Pre-Steady State Kinetic Studies of the Fidelity of *Sulfolobus solfataricus* P2 DNA Polymerase IV. Biochemistry 43, 2106-2115

Fiala, K. A & Suo Z.* (2004) Mechanism of DNA Polymerization Catalyzed by *Sulfolobus solfataricus* P2 DNA Polymerase IV. Biochemistry 43, 2116-2125

Fiala, K. A, Abdel-Gawad, W. & Suo Z.* (2004) Pre-Steady-State Kinetic Studies of the Fidelity and Mechanism of Polymerization Catalyzed by Truncated Human DNA Polymerase Lambda. Biochemistry, accepted and in press.

Allison, A. J., Ray, A., Suo Z., Colacino, J. M., Andeson, K. S., Johnson, K. A. (2001) "Toxicity of Antiviral Nucleoside Analogs and the Human Mitochondrial DNA Polymerase", J. Biol. Chem. 276, 40847-40857.

New drugs are the products of a long and involved drug development process, the first step of which is the discovery of compounds with promising activity. New enzyme inhibitors can be discovered by screening libraries of drug candidate compounds against a target enzyme. Conventional drug screening and validation approaches utilize micro- to milli-scale biochemical or cellular assays to detect downstream biochemical or cellular signatures of enzymatic interference. In view of the limitations of conventional drug screening methods, there remains a need in the art for improved methods and apparatuses for the detection of promising drug candidates.

SUMMARY OF THE INVENTION

The present application discloses methods and apparatuses for single molecule drug screening, discovery and validation. These methods and apparatuses allow a user to detect rapidly, using observation of single molecules, whether and how a drug candidate interferes with a target enzyme involved in a particular disease pathway. The methods and apparatuses described herein utilize single molecule manipulation and detection technologies (e.g., optical or magnetic tweezers) to directly detect whether the characteristic dynamics, or "mechanical signature," of the target enzyme-substrate interaction are substantially altered or modulated by a drug candidate. Furthermore, the methods and apparatuses are useful for analyzing the modulation of the mechanical signature in order to identify potential interference mechanisms of a drug candidate.

In one aspect of the invention, the methods and apparatuses disclosed herein relate to monitoring the real-time dynamic mechanical signatures of individual polymerase molecules (e.g. DNA polymerases, RNA polymerases, and reverse transcriptases) along a polynucleotide substrate in the presence of drug candidates that either inhibit or otherwise modulate the polymerization process. Identification and analysis of such drug candidates is critical for anti-viral, anti-cancer, and antibiotic drug development.

BRIEF DESCRIPTION OF THE DRAWINGS

FIG. 2A shows a representative signal expected from a control sample where no polymerase inhibitor is present. In this scenario, the polymerase binds to single stranded (ss) DNA and converts this template into double stranded (ds) DNA, steadily shortening the overall template length with time. FIG. 2B shows an exemplary mechanical signature expected from an optical tweezers apparatus that would indicate that a drug candidate has slowed the replication process. Note that the overall slope of the template length plot, which corresponds to the polymerization velocity, has lessened. FIG. 2C shows an exemplary mechanical signature from an optical tweezers apparatus that indicates that a drug candidate has induced abortive transcription/premature termination, wherein the drug candidate has derailed or stalled the replication process before its natural completion point. FIG. 2D shows an exemplary mechanical signature from an optical tweezers apparatus that indicates that initiation of DNA replication is inhibited by the drug candidate. FIG. 2E shows an exemplary mechanical signature from an optical tweezers apparatus that indicates the drug candidate induces the polymerase enzyme to operate in an exonucleolysis mode, wherein it excises bases rather than polymerizes base-pairs. This signature would likely only occur in polymerases with an active exonucleolysis, or "proof-reading" site.

FIG. 4, Panel B illustrates additional exemplary experimental geometries for obtaining, via an optical tweezers-based single-molecule measurement system, the length of a nucleic acid as it is processed by a polymerase enzyme. Here a DNA molecule is held immobilized and stretched between a plastic latex bead and a streptavidin-coated (triangles) glass surface. As the polymerase moves along the DNA template in DNA replication, the length of the the DNA tether decreases at a given force as the immobilized template DNA is converted from single to double stranded DNA.

FIG. 4, Panel C illustrates an embodiment of the present invention where the nucleic acid template is attached to a dielectric bead that is held by a second, immobilized optical trap, shown at left, that exerts a strong trapping force that is much greater than the force exerted by the polymerase on the nucleic acid template. Here the polymerase is attached by the relevant affinity chemistry to the other bead.

FIG. 4, Panel D demonstrates how the nucleic acid can be immobilized to a rigid surface, such as a cover slip or microwell plate, via complementary functionalization of the nucleic acid template and the rigid surface, while again the polymerase is attached to the second bead.

In FIGS. 6A and 6B, position of the polymerase along DNA is shown as a function of time. The slope gives the rate of change in length of the DNA template at a given force while it is being replicated. This is just the single molecule velocity of the polymerase motor.

In FIG. 7, the extension (μm) of the DNA is shown versus time (min). In the left plot, the black line shows full data set, including relaxation due to flow (left boxed region) before the contraction (right hand boxed region) begins. At right, extension versus time is shown for the contraction region. The raw data line shows original length-vs-time data, while the smoothed line shows 100-pt adjacent average of this data. The straight line indicates the average slope through this contraction region, about 300 hp/second.

FIG. 9 illustrates key features of the novel drug screening and discovery techniques described herein.

FIG. 10 illustrates some of the advantages of the novel drug screening and discovery techniques described herein as compared to conventional approaches to drug screening and discovery.

DETAILED DESCRIPTION OF EMBODIMENTS OF THE INVENTION

Figure 1:
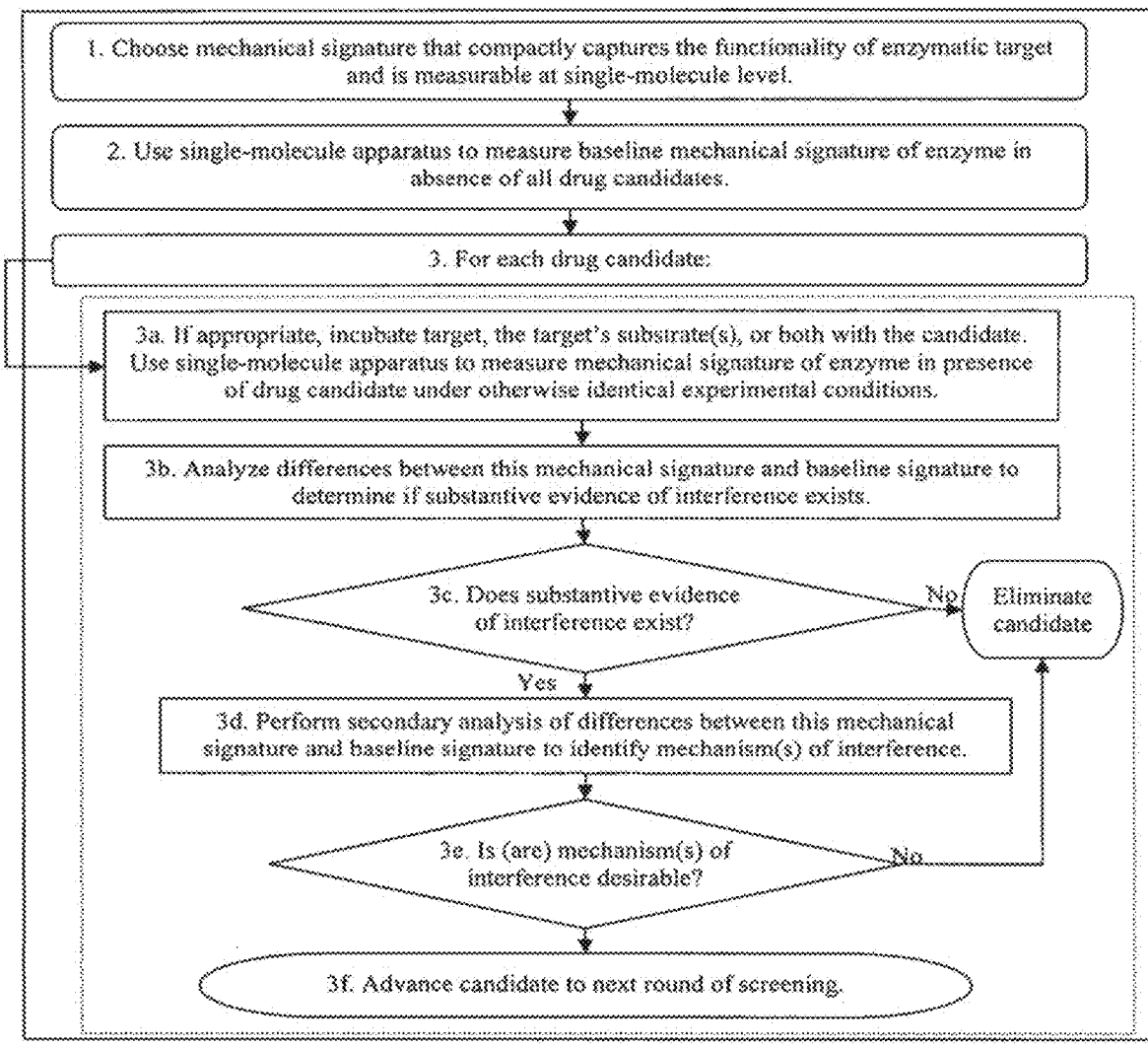
FIG. 1 illustrates exemplary flow charts of a method aspect of this invention for screening multiple drug candidates that target a particular enzyme.

DNA and RNA polymerase and reverse transcriptase (RT) inhibitors are valuable in both clinical and research settings. These inhibitors help in elucidating the mechanistic aspects of transcription and DNA replication, in mapping structure-function relationships, and in characterizing protein activity. These polymerase and RT inhibitors are also among the most attractive drug targets. Knowledge about these inhibitors, their structures, and their mechanisms enable the design of new drugs such as anti-cancer agents and antibiotics that will be effective against new pathogens and antibiotic-resistant mutants of known pathogens. Because some of these inhibitors have been reported to induce and/or inhibit apoptosis, they also provide valuable tools for investigating apoptosis. Likewise, because some of these agents block specific steps of DNA transcription, polymerase inhibitors can help to elucidate the role of transcriptional control in regulating the expression of target genes in various healthy and disease states.

Drugs that target polymerase proteins involved in a particular disease pathway are well known in the art. Reverse transcriptase inhibitors (RTIs), for example, are a class of antiretroviral drugs that target construction of viral DNA by inhibiting the activity of reverse transcriptase. There are two subtypes of RTIs with different mechanisms of action: nucleoside and nucleotide analogue RTIs are incorporated into the viral DNA leading to chain termination, while non-nucleoside-analogue RT is act as competitive inhibitors of the reverse transcriptase enzyme. Current AIDS therapeutics that function by inhibiting HIV reverse transcriptase are described in the art (see, e.g., Bean et al., Appl Environ Microbiol 72:5670-5672 (2005)), and include Efavirenz (brand names SUSTIVA® and STOCRJN®) and Nevirapine (also marketed under the trade name VIRAMUNE®).

Many drugs have been found to be efficacious in the treatment of cancer. These include diverse chemical compounds such as antimetabolites (e.g., methotrexate and fluorouracil), DNA-damaging agents (e.g., cyclophosphamide, cisplatin, and doxorubicin), mitotic inhibitors (e.g., vincristine), nucleotide analogues (e.g., 6-mercaptopurine), inhibitors of topoisomerases involved in DNA repair (e.g., etoposide), inhibitors of DNA polymerase (e.g., bleomycin), or intercalating agents like mitoxantrone.

Several drugs targeting enzymes of mammalian DNA replication are currently being investigated as promising candidates for cancer chemotherapy or as probes for understanding the roles of specific enzymes in DNA replication and repair. These potential drug candidates include, but are not limited to corylifolin, bakuchiol, resveratrol, Neobavaisoflavone, and daidzein (see Sun et al., J. Nat. Prod. 61, 362-366 (1998).

Other examples of DNA and RNA Polymerase Inhibitors include: Actinomycin D, *Streptomyces* sp.; a-Amanitin, *Amanita* sp.; Aphidicolin; HSV Replication Inhibitor, BPS; Methyl a-Amanitin Oleate; Novobiocin, Sodium Salt; Rifampicin; RNA Polymerase III Inhibitor; Actinomycin D, 7-Amino. Three polymerase inhibitors currently in Phase II trials for use against Hepatitis C Virus are Idenix/Novartis' valopicitabine (NM283); ViroPhanna's HCV-796 and Roche's R1626. Roche/Idenix are also investigating valtorcitabine (val-LdC)—a first strand viral DNA synthesis inhibitor in Phase II HCV trials after initial success as an HBV treatment.

DNA damaging agents provide some of the most successful treatments for cancer. The enzyme Poly (ADP-ribose) polymerase (i.e. PARP) can help repair DNA damage caused by the DNA damaging agents used to treat cancer a. As PARP activity is often increased in cancer cells, it provides these cells with a survival mechanism. ABT-888, for example, is an oral PARP-inhibitor developed by Abbott Oncology to prevent DNA repair in cancer cells and increase the effectiveness of common cancer therapies such as radiation and alkylating agents. Moreover, preclinical data indicates ABT-888 has improved the effectiveness of radiation and many types of chemotherapy in animal models of cancer.

New drugs are the products of a long and involved drug development process, the first step of which is the discovery of compounds with promising activity. New enzyme inhibitors can be discovered by screening libraries of drug candidate compounds against a target enzyme. Drug candidates include compounds found in nature, compounds synthesized by combinatorial chemistry approaches, and compounds created via rational drug design. Conventional drug screening and validation approaches utilize micro- to milliscale biochemical or cellular assays to detect downstream biochemical or cellular signatures of enzymatic interference. For example, an assay might, via radioactive labeling, measure any changes in the quantity of a reaction product whose synthesis is catalyzed by the target enzyme.

Single-molecule techniques offer several key benefits over conventional in vitro assay methods for drug screening, as they use less reagents and offer much more detail into the mechanism of drug action on the target. For example, single molecule techniques enable transient states to be observed, thereby making it possible to selectively screen for chemical compounds that isolate these steps. Single molecule approaches thus enable the identification, testing, and validation of polymerase or enzyme inhibitors that target key phases in biochemical processes, e.g., transcription or replication initiation. Many biochemical processes consist of multiple transient steps, such as promoter binding, initiation, elongation, and termination in transcription. Because the total number of potential drug targets can be extremely high, single molecule approaches provide a critical advantage in speeding up the process of drug screening and discovery by focusing the efforts early on to only those steps of the process that are most affected by the drug candidate.

By elucidating the kinetic mechanisms of enzymes involved in DNA/RNA replication and repair, antiviral and anti-cancer drug candidates can be identified based on rational drug design. Kinetic studies use a variety of pre-steady state kinetic methods including rapid chemical quench-flow and stopped-flow techniques. These methods allow reactions to be quenched in milliseconds, and provide more kinetic information than the traditional steady-state kinetic methods. Single molecule techniques elucidate the elementary steps of reactions occurring at the active sites of enzymes and can significantly enhance rational drug design.

Fears about the possible release of smallpox by bioterrorists have led to intensive efforts to find an effective molecule to inhibit viral infection which does not yet exist. Since smallpox virus (variola virus) and the smallpox vaccine (vaccinia virus) are highly homologous, the latter has been used as a very good surrogate model. Vaccinia virus DNA polymerase, for instance, is about 99% identical to in the polymerase in the small poxvirus.

The Hepatitis C virus has infected at least 2-3% of human population. Viral genome replication has been intensively studied. The RNA-dependent RNA polymerase, NS5B, is central to viral replication, and is a major antiviral drug target. Although there are extensive biochemical and steady-state kinetic studies on this polymerase, the elementary steps of nucleotide incorporation catalyzed by NS5B are still undefined. These investigations enable the rational design of nucleoside inhibitors.

In the last decade, new tools (for example optical tweezers, atomic-force-microscopy, and small glass fibers) have been developed to manipulate small objects and also to investigate the forces involved in the systems studied (see, e.g., Smith et al., Science 271:795 (1996) and Cluzel, et al., Science 271, 792-794 (1996)). In particular, optical or magnetic "tweezers" or "traps" trap particles with forces generated by optical intensity gradients, and can be used to manipulate and study microscopic molecules at the single-molecule level. Optically generated forces strong enough to form a three-dimensional trap can be obtained by bringing a laser beam with an appropriately shaped wavefront to a tight focus with a high numerical aperture lens. The principles of optical trapping are well known in the art and are summarized in, for example, Neuman and Block, Rev. Sci. Instr. 75:2787-2809 (2004).

In the biological sciences, optical tweezers have been used to measure displacements in the nm range of molecules ranging in size from 10 nm to over 100 mm. Common to most optical tweezers biophysical experiments is the attachment of dielectric beads to biological molecules (e.g. substrates and/or enzymes), so that the biological molecules can be manipulated by the optical trap and mechanical measurements can be taken. Various biochemical and molecular biology methods are known in the art for attaching nucleic acids, other substrates, enzymes and other biomacromolecules to functionalized surfaces and beads. For example, DNA can be labeled with biotin moieties that will bind to commercially available, streptavidin-coated, micron-coated dielectric spheres (e.g., from Bangs' Laboratories).

Two of the main uses for optical traps in biology have been the study of the physical properties of DNA, and the study of molecular motors such as DNA and RNA polymerases ((see, e.g., Davenport et al., Science 287:2497-2500 (2000); Maier et al., PNAS 97:12002-12007 {2000); Wang et al., Science 283:902-907 (1998); Wuite et al., Nature 404:103-106 (2000); and Yin et al., Science 270:1653-1656 (1995)). For example, researchers have been able to measure the sequence-dependence of the forces necessary to "unzip" double-stranded DNA (Voulgarakis, et al., Nano Letters 6, 1483-1486 (2006)). In addition, optical tweezers were used to elucidate the mechanism whereby kinesin walks along a microtubule (Kuo & Sheetz, Science 260,232 (1993) and Block, et al., Nature 348, 348-352 (1990)). Quite recently, researchers detected with single base-pair resolution the stepping action of the RNA polymerase along a molecule of DNA (Abbondanzieri, et al., Nature 438, 460-465 (2005)). At Nanobiosym, high-resolution optical tweezers have been utilized to experimentally demonstrate the role of various environmental factors on the dynamics of polymerases (Goel et al, Nature Nanotechnology review article in press).

In all such studies, optical tweezers were utilized to directly measure the mechanical dynamics of a substrate-enzyme interaction. In these studies, the details of experimental setup and measurements taken are dependent on the biological function of the enzyme and/or the substrate involved. For example, the mechanical measurements of interest may include: the elasticity of substrate polymers, including stretching and relaxation dynamics; the time dependent velocity of an enzyme that is "processing" a linear substrate, such as polymerase bound to a nucleic acid; the deformation of a substrate caused by enzymatic binding; and/or the efficiency or accuracy of substrate binding and processing. By integrating position and/or force-sensing subsystems into an optical tweezers apparatus, all such measurements are possible.

Novel methods and apparatuses for single molecule drug screening discovery and validation are disclosed herein. These methods and apparatuses allow a user to detect rapidly, at the single-molecule level, whether and how a drug candidate interferes with an enzyme-substrate interaction involved in a particular disease pathway. In particular, interactions between candidate drugs and a single target enzyme molecule can be observed. The methods and apparatuses described herein utilize single molecule manipulation technologies (e.g. optical or magnetic tweezers or traps) to directly detect, at the single-molecule level, whether a drug candidate can mechanically or chemically alter the enzyme-substrate interaction.

In a preferred embodiment, the present methods and apparatuses can be utilized to quickly screen, test, and validate new drug candidates that modify, inhibit or otherwise interfere with polymerase enzymes such as DNA polymerase, RNA polymerase, and RNA reverse transcriptase, etc., and to better elucidate the mechanism whereby the polymerase/substrate interaction is inhibited.

Normal enzymatic activity on a substrate produces a dynamic "mechanical signature." The term "mechanical signature" as used herein refers to the biomechanical trace of a single molecule of an enzyme as it interacts with it's substrate. The biomechanical trace can be measured using instruments, such as optical tweezers, that can detect displacements in the nm range. As described above, this dynamic mechanical signature can be determined by making a "mechanical measurement," for example by measuring changes in the elasticity of substrate polymers, including stretching and relaxation dynamics; the time-dependent velocity of an enzyme that is "processing" a linear substrate, such as polymerase bound to a nucleic acid; the deformation of a substrate caused by enzymatic binding; and/or the efficiency or accuracy of substrate binding and processing.

The term "mechanical measurement" as used herein means a measurement of the mechanical dynamics of a substrate-enzyme interaction, wherein the mechanical measurement detects the mechanical signature of a single molecule of a target enzyme and/or a single molecule of a substrate of the target enzyme. "Making a mechanical measurement" includes, for example, measuring changes in the elasticity of substrate polymers, including stretching and relaxation dynamics; the time-dependent velocity of an enzyme that is "processing" a linear substrate, such as polymerase bound to a nucleic acid; the deformation of a substrate caused by enzymatic binding; and/or the efficiency or accuracy of substrate binding and processing.

A preferred "mechanical measurement" is a measurement of the movement of a reverse transcriptase, DNA polymerase, or RNA polymerase enzyme along a polynucleotide (e.g. DNA or RNA) substrate. Thus, in particular embodiments of the method, discussed in more detail below, the real-time single molecule dynamics of a polymerase along a nucleic acid sequence is monitored in the presence and absence of drug candidates via optical trapping techniques. Other mechanical measurements of a polymerase/substrate interaction which are not explicitly described herein but are also measurable via single molecule detection techniques (e.g. optical tweezers) are also possible.

A mechanical measurement can be made in the presence or absence of a drug candidate. A "baseline mechanical signature" is a mechanical signature that was determined via a mechanical measurement that was made in the absence of a drug candidate.

The term "target" or "drug target" as used herein refers to a biomolecule that is involved in a disease pathway. Inhibiting or otherwise interfering with the activity of the target could be beneficial in treating and/or preventing the disease. The term "target enzyme" as used herein refers to an enzyme that is involved in a disease pathway. Typically a target enzyme is a key enzyme involved in a particular metabolic or signaling pathway that is specific to a disease condition or pathology, or to the infectivity or survival of a microbial pathogen. The "activity of a target enzyme" means the interaction of the target enzyme with a substrate of the target enzyme.

Target enzymes suitable for the present invention include enzymes that bind to and interact with DNA and/or RNA. Examples include polymerases, such as DNA polymerases, RNA polymerases, and reverse transcriptases; topoisomerases; gyrases; exoncucleases; and helicases. The target enzymes can be human enzymes, for example human enzymes involved in a disease pathway such as cancer. In another embodiment, the target enzymes can be viral or bacterial enzymes, such as viral or bacterial enzymes involved in viral- and/or bacterial mediated diseases. Other microbial enzymes are also contemplated as target enzymes suitable for the present invention.

A preferred target enzyme is a polymerase enzyme such as a DNA polymerase, an RNA polymerase, or a reverse transcriptase. Polymerases involved in cancer pathways, especially human DNA polymerases involved in human cancer pathways, are particularly preferred. Polymerases involved in viral-mediated disease pathways, especially viral reverse transcriptases involved in viral-mediated disease pathways in humans (e.g. hepadnaviral reverse transcriptases such as Hepatitis B reverse transcriptase, and retroviral reverse transcriptases such as HIV-1 reverse transcriptase) are also particularly preferred.

The present invention is also suitable for screening drug candidates that may interact with non-enzyme targets involved in disease pathways. Representative examples of non-enzyme targets are microtubules and ribozymes (such as ribosomes). Ribosomes, in particular, use RNA as a template to build polypeptide chains, and thus can be thought of as a giant enzymes.

The term "substrate of the target enzyme" (or "enzyme substrate" or "substrate") as used herein refers to a molecule upon which a target enzyme acts. Enzymes catalyze chemical reactions involving one or more substrates. Enzyme substrates are well known in the art.

Preferred substrates include polymerase substrates, such as polynudeotides (e.g. DNA and RNA). Polynucleotide substrates are also referred to herein as polynucleotide or nucleic acid "templates." Polynucleotide substrates can be double-stranded or single-stranded DNA or RNA sequences.

The term "drug candidate" or "candidate" as used herein refers to a compound that may inhibit or otherwise interfere with the activity of a target, particularly a target enzyme. Drug candidates include compounds found in nature, compounds synthesized by combinatorial chemistry approaches, and compounds created via rational drug design. Examples of drug candidates include compounds that interact with or may interact with polynucleotides (e.g. DNA and/or RNA), and/or compounds that interfere with or may interfere with the activity of enzymes that interact with polynucleotides. Such compounds can be known or potential DNA modifying agents, including DNA damaging agents (e.g. intercalating agents that interfere with the structure of nucleic acids); DNA bending agents; mismatch binding proteins; and/or alkylating agents.

In another embodiment, a drug candidate can be a compound that interacts with or may interact with a non-enzyme target involved in disease pathway. Examples include compounds that interact with or may interact with microtubules and/or ribosomes.

Some exemplary classes of drug candidates that can be probed via the present methods are described next. First, several classes of antibiotic drugs are suitable for interrogation by the present methods, including drugs that inhibit or otherwise interfere with the activity of bacterial polymerases such as bacterial DNA polymerase, bacterial RNA polymerase (e.g., rifampin), and/or bacterial reverse-transcriptase. Second, the present methods could also be utilized to quickly screen, test, and validate new antiviral drug candidates that inhibit or somehow interfere with viral polymerases, especially viral reverse transcriptases (e.g. efavirenz and nevirapine), and to better elucidate the mechanism whereby the RNA-reverse transcriptase interaction is inhibited. Third, several classes of anti-cancer drugs are also suitable for interrogation by the present methods. These include drugs that inhibit or otherwise interfere with the activity of DNA polymerases, RNA polymerases, topoisomerases, ribosomes, and/or microtubules (e.g. microtubule antagonists such as vincristine and taxol). Additionally, entirely new drug mechanisms, heretofore unknown, could be discovered and elucidated by the approach described herein.

The term "single molecule detection apparatus" (or "single molecule detection device") as used herein refers to an apparatus that can be used to make a mechanical measurement of an enzyme-substrate interaction at the single-molecule level. Single molecule detection apparatuses suitable for the present invention include apparatuses used for magnetic or optical trapping (e.g. optical tweezers), high-resolution fluorescent imaging coupled with quantum-dot labeling, and atomic force microscopy. Other apparatuses and variants of the apparatuses disclosed herein could be readily envisioned.

A preferred single molecule detection apparatus is an apparatus comprising an optical trap or tweezers.

Instead of screening for a downstream effect of enzymatic interference, the methods described herein, dubbed NANO-VALID™, determine via direct, single-molecule observation if a drug candidate alters the normal "mechanical signature" of the target enzyme. Further, the methods described herein enable the analysis and determination of the mechanism(s) by which the enzymatic dynamics are affected. The methods utilize single molecule manipulation, detection and analysis apparatuses, to determine if and how the drug candidate modulates this "mechanical signature" in away indicative of enzymatic inhibition.

The first step in the NANO-VALID™ screening process is to choose a mechanical signature that captures the functionality of the target enzyme and is reliably measurable at the single molecule level. Exemplary signatures appropriate for specific classes of enzymes that may be extracted with single-molecule detection and manipulation technologies are discussed below in greater detail. The second step in the NANO-VALID™ method is to experimentally determine the normal, baseline mechanical signature of the target enzyme in the absence of any inhibitor, including a drug candidate. As discussed above, the baseline mechanical signature is determined by making a mechanical measurement using a single molecule detection apparatus. Due to the single-molecule nature of the approach, this may involve taking ensemble averages of several experiments. Exemplary technologies and apparatuses that enable single-molecule mechanical measurement of the dynamics of several classes of enzymes are discussed below.

To screen each drug candidate, the chosen mechanical measurement of the target enzyme is made with the same experimental techniques and apparatus and under the same conditions as those used in determining the baseline mechanical signature, except the drug candidate is present in the single-molecule assay. Depending on the nature of the target enzyme, it may be desirable to first incubate the target, the target's substrate(s), or both, with the drug candidate for some controlled period of time prior to conducting this measurement.

Next, extensive signal processing is conducted to compare the candidate-specific mechanical signature with the baseline mechanical signature. Exemplary variants of this analysis appropriate for various classes of enzymes are discussed in detail below. If no significant deviation from the signature is detected, the candidate is rejected and not subjected to further screening. This feature drastically reduces the time and cost associated with drug candidate screening, testing, and validation, because unsuccessful drug candidates can be eliminated from testing much earlier in the process, much before the onset of expensive clinical trials. This leads to much more specific drug candidates being chosen earlier on, such that only those candidates that are more likely to be successful make it to clinical trials. This increased selectivity criterion early on in the drug discovery process significantly reduces the cost and time of single molecule drug discovery processes as compared to conventional drug validation and discovery approaches.

However, if a significant deviation from the baseline mechanical signature is detected, further analysis and processing is conducted to identify potential mechanism(s) of interference. The particular embodiments of this secondary analysis appropriate for various classes of enzymes as discussed in detail below. If the identified mechanism(s) are not desirable for the disease pathway, the candidate is rejected and not subjected to further screening. Otherwise, the candidate is considered for further screening and validation.

This NANO-VALID™ process is summarized in FIG. 1.

NANO-VALID™ for Polymerase Targets

Figure 3:
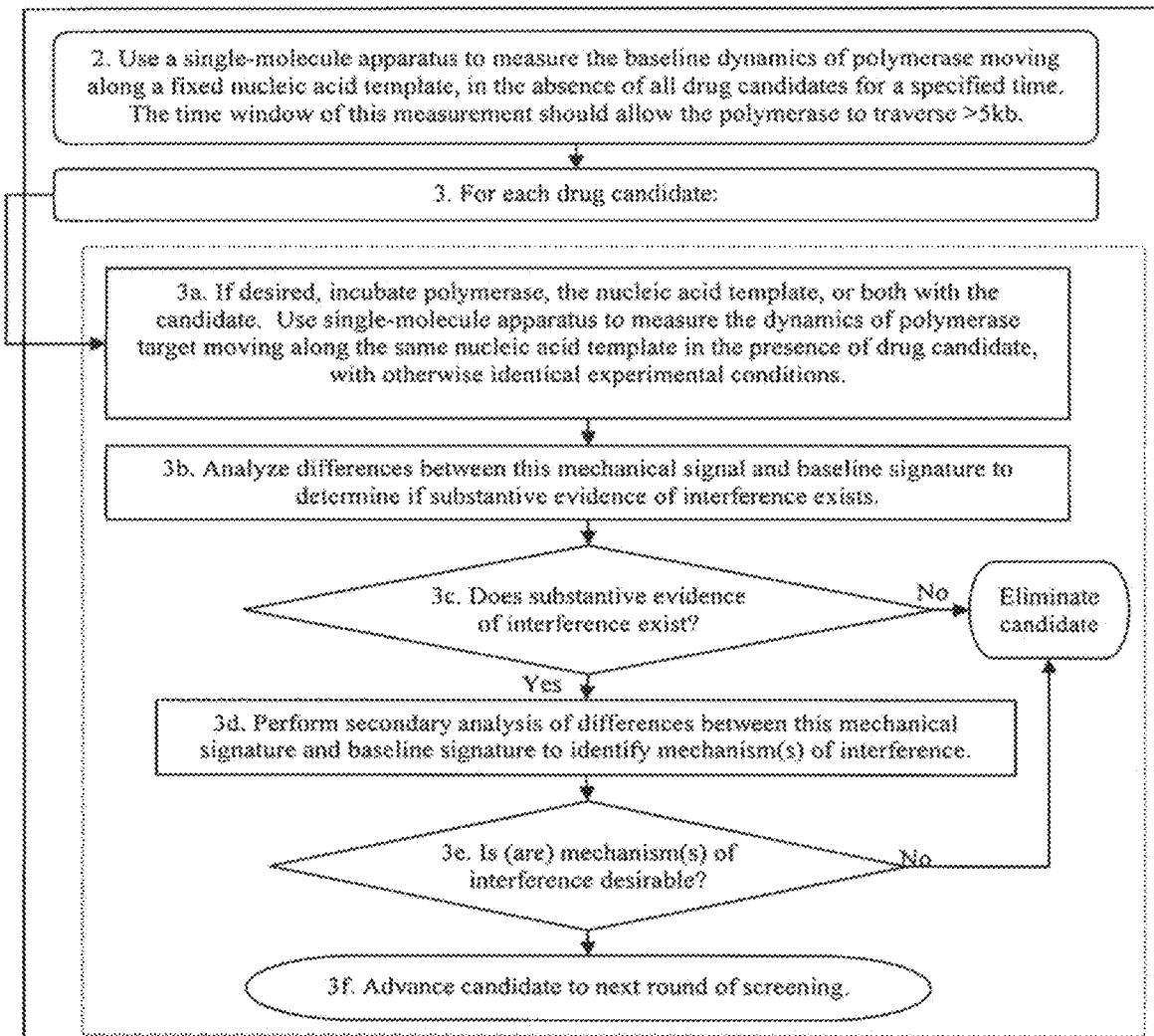
FIG. 3 illustrates exemplary flow charts of a method aspect of this invention for screening multiple drug candidates that target a particular polymerase enzyme, including DNA and RNA polymerase inhibitors and reverse transcriptase inhibitors.

A preferred embodiment of the NANO-VALID™ method that is appropriate for screening drug candidates that target polymerase enzymes. The embodiment is summarized in FIG. 3. In this method embodiment, the time-dependent position of the polymerase enzyme along the nucleic acid template is always chosen at step 1 to be subsequently measured in steps 2 and 3a.

Polymerases process a nucleic acid template in a primarily linear fashion. For this reason, the mechanical signature common to all polymerases is the linear progression of the polymerase along this substrate. When the nucleic acid template is aligned with a fixed line and held at constant tension, then the progression of the polymerase correlates simply to the position of the polymerase along this fixed line as a function of time.

In the absence of an inhibitor, a polymerase normally binds at an initiation point, proceeds with a relatively constant velocity and then terminates polymerization. Some minor stochastic behavior typically occurs during the course of normal polymerization. These features may include short pauses on the order of milli-seconds or less, short reversals of direction on the order of less than 100 bases (20-55 nanometers, depending on the experimental conditions), and variations in the polymerization velocity on the order of a few hundred base pairs-per second.

Figure 6A:
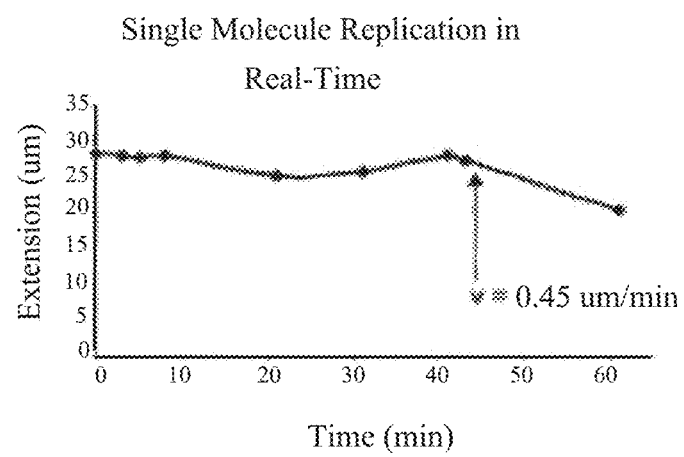
FIGS. 6A and 6B illustrate data demonstrating the capability to observe the dynamics of the DNA polymerase motor with an optical tweezers apparatus as it moves forwards (polymerization, FIG. 6A and backwards (exonuclease activity, FIG. 6B) along a DNA template. A velocity of about 0.5 microns/minute corresponds to about 25 basepairs polymerized/second.
Figure 6B:
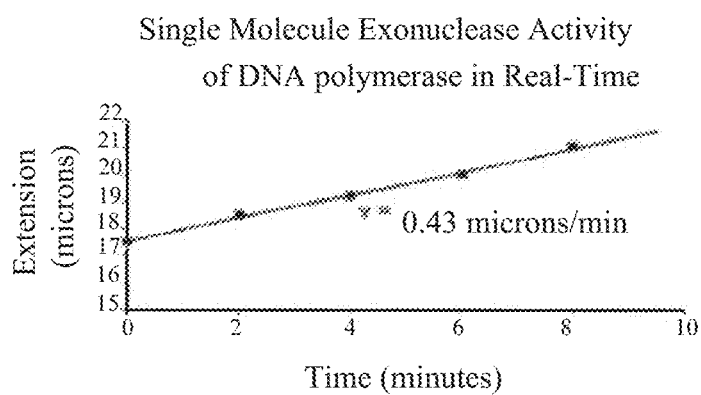
Figure 7:
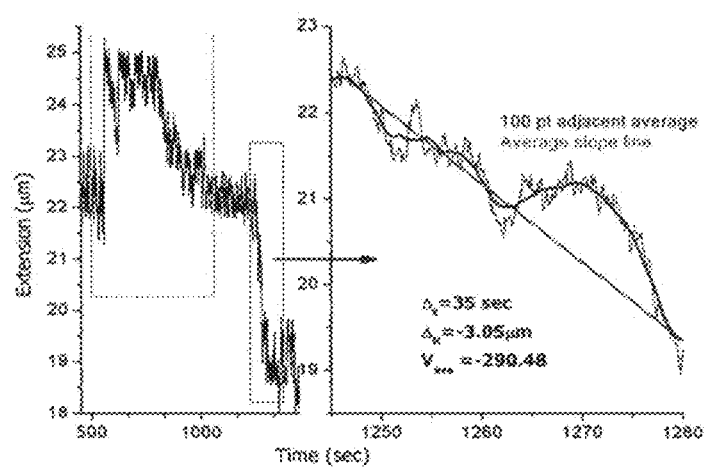
FIG. 7 illustrates the ability to probe even fine-structure dynamics of DNA polymerization. To achieve this level of resolution, an acousto-optic deflector system is preferably utilized to achieve isotension conditions along the DNA strand during polymerization.

Shown in FIG. 6 are data demonstrating the capability to observe the dynamics of the DNA polymerase motor with an optical tweezers apparatus as it moves forwards (polymerization) and backwards (exonuclease activity) along a DNA template. A velocity of about 0.5 microns/min corresponds to about 25 base-pairs polymerized/second. Without wishing to be bound by theory, it is surmised that polymerase inhibitors impact DNA polymerases (DNAp) through one of several mechanisms, each with a distinct "mechanical signature" in the plot of template length versus time, and/or the velocity of polymerization versus time. The plots can be analyzed to identify the mechanisms. Additionally, there may be other entirely new mechanisms, hereto unforeseen that could also be discovered via our methods described herein.

Figure 2A:
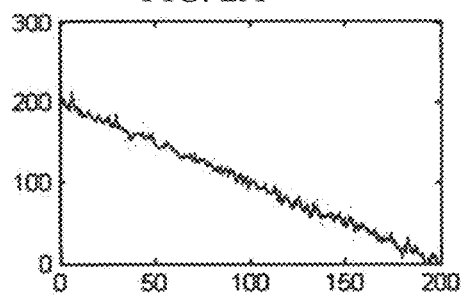
FIGS. 2A-2E illustrates exemplary mechanical signatures from DNA polymerase in the presence of various drug candidates (such as polymerase inhibitors).
Figure 2B:
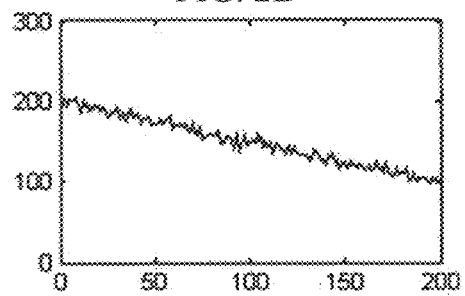
Figure 2C:
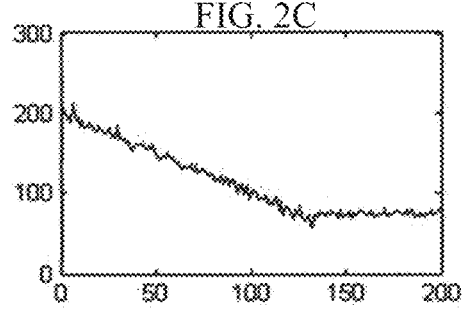
Figure 2D:
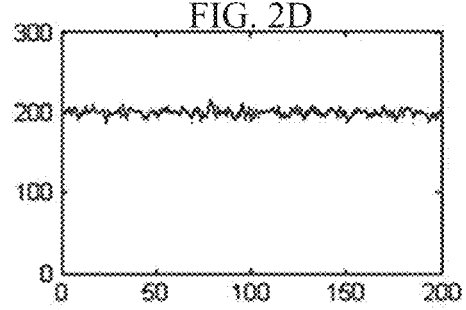
Figure 2E:
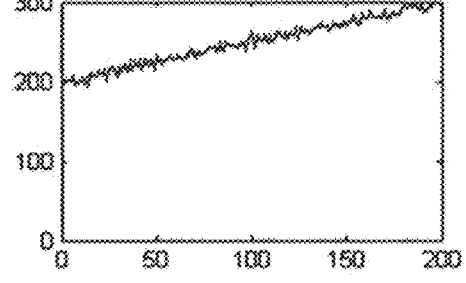

FIGS. 2A-2E illustrate what polymerization might look like in the presence or absence of a drug candidate. Note that for FIGS. 2A-2E shown, the initiation point is a y=200 μm and the polymerase is presumed to be moving from right (y=200 μm) to left (y=0 μm) in about 200 minutes. When a drug candidate interferes with a polymerase target, the dynamics of the polymerase along a nucleic acid template are clearly affected in one of several ways, which may include: modulating the rate of polymerization, inactivating the enzyme from binding or polymerizing, altering the processivity of the enzyme, altering the binding affinity of the enzyme to the template, or altering the sequence-dependent fidelity of the enzyme. Each of these scenarios produces a mechanical signature distinct from normal polymerization. Thus this preferred embodiment of the NANO-VALID™ method for polymerase targets uses the time-dependent position of the enzyme as the mechanical signature in steps 2 and 3a (see FIG. 3, NANO-VALID™ Drug Screening and Validation process map). FIG. 2B shows an exemplary mechanical signature that would indicate that a drug candidate has slowed the polymerization process. Note that the average slope of the plot, which corresponds to the average polymerization velocity, has lessened. Some DNA polymerase inhibitors may work, for example, by just slowing the overall speed of DNA replication. This trace would indicate a polymerase inhibitor drug candidate that worked by this mechanism. FIG. 2C shows an exemplary mechanical signature that indicates that a drug candidate has induced premature termination, wherein the drug candidate has derailed or stalled the polymerization process before its natural completion point. Some DNA polymerase inhibitor candidates may work by such a mechanism. This trace would indicate a polymerase inhibitor drug candidate that worked by this mechanism. FIG. 2D shows an exemplary mechanical signature that indicates that initiation of the polymerase is inhibited by the drug candidate. This trace would indicate a polymerase inhibitor drug candidate that worked by this mechanism. FIG. 2E shows an exemplary mechanical signature that indicates the drug candidate induces the polymerase enzyme to operate in an exonucleolysis mode, in which it excises bases rather than polymerizing base-pairs. This signature would likely only occur in polymerases with an active exonucleolysis, or "proof-reading" site. This trace would indicate a polymerase inhibitor drug candidate that worked by this mechanism.

To avoid false screening results, the mechanical signature used in this embodiment of the NANO-VALID™ method should be on a length- and time-scale that far exceeds the scale of the stochastic events of normal polymerization. Typically, for most polymerases, the mechanical signature should be taken over a time window that will allow the target, under the chosen experimental conditions, to traverse a nucleic acid template of at least 5000 bases or base-pairs.

In a preferred embodiment, a software algorithm to implement step 3b is utilized so that it may determined with high accuracy in step 3c if a drug candidate should be eliminated.

The stochastic nature of normal polymerization requires extraction of the salient features of the polymerase dynamics in steps 2 and 3a, rather than using or comparing raw data traces. The nature of the target enzyme, as well as the desired interference mechanisms will dictate which salient features are extracted and analyzed. These features may include: total time the motor is paused, terminal polymerization velocity, efficiency of termination, average velocity. Typically, for all polymerases, a low-pass filter with a cutoff frequency of 100-1000 Hz will also be applied to the raw signal to filter out the effects of the stochastic fluctuations in the dynamics of the enzyme.

NANO-VALID™ for DNA Polymerase Targets using Template Length Measurements A variant embodiment of the previously described NANO-VALID™ method that is appropriate for DNA polymerase targets that act on a single-stranded DNA template. Each base in the single-stranded DNA template has a length of approximately 0.7 nm under standard environmental conditions and a constant template tension of approximately 0-1 pN. Each unpaired base on the template is converted by the DNA polymerase into a base-pair with a length of approximately 0.34 nm under the same environmental and constant-tension conditions. Hence, under isotension conditions, as the DNA polymerase replicates the linear template, converting single-stranded DNA into double stranded DNA, the difference in elasticity of the two states causes a shortening of the DNA strand by approximately 0.36 nm per base-pair that is polymerized at a given force. Thus, tracking the length of the DNA strand during polymerization under constant DNA template tension is analogous to tracking the position of a polymerase along a fixed template. Therefore, in steps 2 and 3a of this method variant, the mechanical signature directly obtained by the single-molecule measurement apparatus is the length of the DNA template over time. The signal processing methods described previously for analyzing a polymerase's position and velocity in steps 3b and 3d can again be utilized in this variant method.

Apparatus for Performing NANO-VALID™ Screening of Drug Candidates

An apparatus aspect of this invention for performing the NANO-VALID™ method comprises a single-molecule measurement system interfaced to a personal computer via a rapid port (e.g., a USB port) that allows near real-time data-acquisition and control of the single-molecule apparatus system. See FIGS. 9A and 9B. Via software drivers, this apparatus is controlled and interrogated by a custom software program that has a graphical user interface (GUI). In this embodiment, the single-molecule measurement system would have a receptacle for loading and addressing several individual samples on a single plate, for example a 96-well microplate. The measurement system would integrate temperature controls to ensure reliable and reproducible environmental conditions. The measurement system could comprise one or more of the following: atomic force microscope, scanning electronic microscope, etc, etc.

To utilize the apparatus, the user would load the plate into the single-molecule measurement. Via the GUI, they would initialize the single-molecule measurement system, including any necessary calibrations. The user would then select the mechanical signature, and any control parameters regarding the signature (for example the length of time that the signature is measured). Next, via the GUI, they would direct the single-molecule measurement system to interrogate the control samples to obtain the target enzyme's baseline mechanical signature. The precise execution of this measurement might require some manual control and input from the human user via keyboard, joystick or other computer input device. The custom software program would then acquire this signature, and via signal-processing routines, extract and store salient features of the signal. The GUI would display the salient features, including perhaps the raw mechanical signature traces.

Next, the GUI would allow the user to traverse the remainder of the plate, to acquire a mechanical signal from each candidate; this may entail several individual measurements. As before, this signature acquisition step might require direct user input. At each step, the raw mechanical signature would be acquired, salient features of the mechanical signature would be extracted via signal processing, stored in the computer memory and displayed to the user, and compared to the reference baseline signal.

Apparatuses for Performing NANO-VALID™ Screening of Drug Candidates Targeting a Polymerase To perform the NANO-VALID™ method for polymerase targets, it is necessary that the single-molecule measurement apparatus accurately capture the real-time dynamics of the polymerase along a nucleic acid template. Several technologies could be utilized to accomplish this functionality. For example, high-resolution fluorescent imaging coupled with quantum-dot labeling of the polymerase could be utilized.

Alternatively, atomic force microscopy could be utilized to measure these polymerase dynamics. Magnetic or optical "tweezers" or "traps" could also be utilized for pico-Newton control of the template tension and measurements of nanoscale displacements of the polymerase along the DNA template. Other variants could be readily envisioned.

Optical Tweezers-Based Apparatuses for Performing NANO-VALID™ Screening of Drug Candidates Targeting a Polymerase In a preferred embodiment, the NANO-VALID™ apparatus for polymerase targets would utilize an optical tweezers-based single-molecule measurement subsystem. An optical tweezers traps particles with forces generated by optical intensity gradients. Optically generated forces strong enough to form a three-dimensional trap can be obtained by bringing a laser beam with an appropriately shaped wavefront to a tight focus with a high numerical aperture lens. Optical tweezers techniques have been used extensively for single-molecule studies of the polymer properties of DNA and the force-dependent kinetics of biomolecular motors, including polymerase enzymes. As a result of these extensive biophysical studies, the experimental protocols for using optical tweezers to track polymerase enzymes along an isotension nucleic acid template are quite mature and well-known in the art (Block, et al., Nature 348, 348-352 (1990) and Wuite et al., Nature 404: 103-106 (2000)).

To track the polymerase along the template, one end of the nucleic acid template is effectively immobilized, while the polymerase molecule is attached to a bead trapped in an electronically-steerable optical tweezers apparatus. As the polymerization proceeds, the optical trap is designed to automatically move in order to maintain constant force on the polymerase's bead. The dynamic position of the trap under these isotension conditions then correlates then to the dynamics of the polymerase along the template during polymerization. A preferred embodiment of this "Force-Feedback Optical Trapping Subsystem" is described in extensive detail below. Several other variants could be readily imagined.

Figure 4:
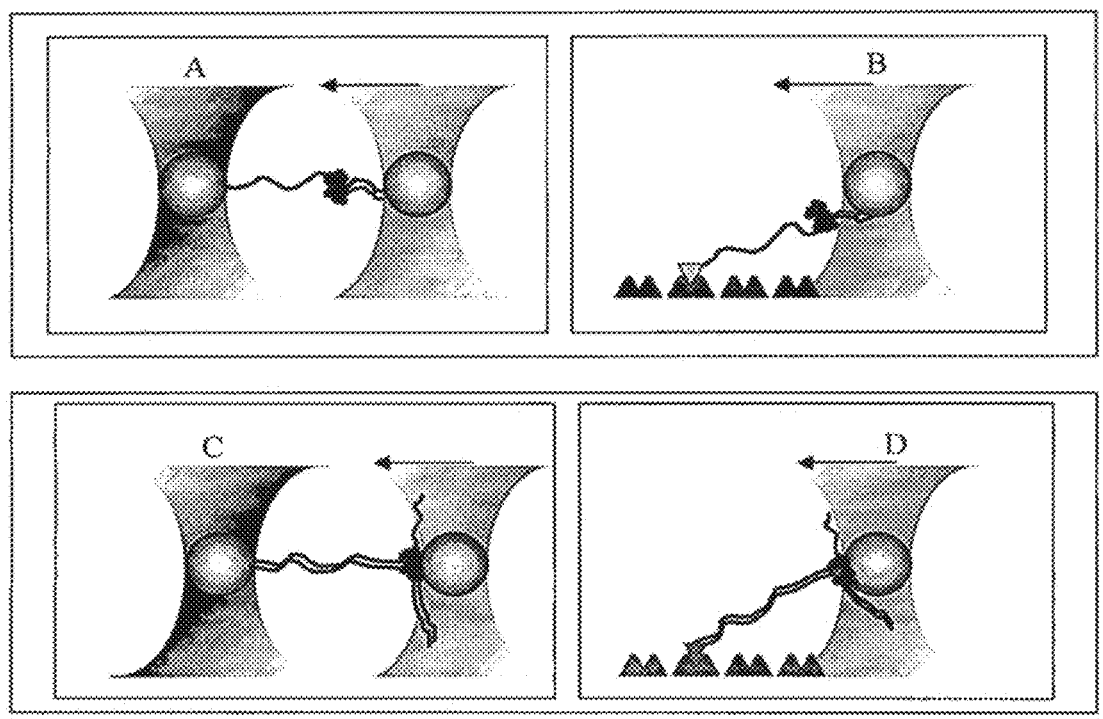
FIG. 4, Panel A illustrates exemplary experimental geometries for obtaining, via an optical tweezers based single-molecule measurement system, the measurement of a polymerase's position along a nucleic acid template template. Here a DNA molecule is held immobilized and stretched between two plastic latex beads, as the polymerase moves along the DNA template. In the case of DNA replication, the distance between the two beads decreases at a given force as the template DNA is converted from single to double stranded DNA. The methods of attachment of the nucleic acid to the beads can be via streptavidin-biotin, or dig-anti-dig, or other covalent linkages.

FIG. 4 shows experimental variants of this embodiment; they vary in their method of nucleic acid immobilization. In FIG. 4C the nucleic acid template is attached to a dielectric bead that is held by a second, immobilized optical trap, shown at left, that exerts a strong trapping force that is much greater than the force exerted by the polymerase on the nucleic acid template. FIG. 4D demonstrates how the nucleic acid can be immobilized to a rigid surface, such as a cover slip or microwell plate, via complementary functionalization of the nucleic acid template and the rigid surface.

Methods for attaching nucleic acids and polymerases to beads or other surfaces are well known in the art; some examples given below illustrate exemplary methods for accomplishing this task. One such method biotinylates the nucleic acid or polymerase via standard methods so that it may be attached to streptavidin-coated microbeads (e.g., Bang's Laboratories) or streptavidin-coated coverslips (e.g., Xenopore Corporation).

Optical Tweezers-Based Apparatuses for Performing NANO-VALID™ Screening via Single-Molecule Measurement of Nucleic Acid Template Length The previously described preferred apparatus embodiment can be used to perform the variant NANO-VALID™ method used for DNA polymerases along a single-stranded DNA template. As previously discussed, this method variant measures the length of the DNA template, instead of directly tracking the polymerase motion. To conduct this method variant, one end of the DNA must be immobilized as before; however, the other end of the DNA template is now attached to a dielectric bead that is interrogated by the steerable, constant-force optical trap. The enzyme remains free in solution.

In this variant method, instead of the trap moving in response to the force of the polymerase enzyme moving along the template, it will move to maintain constant force on the DNA template, even as the template molecule shortens as a result of polymerization. As discussed previously, this is a nearly analogous measurement. While the method variant requires slight differences in the sample preparation, this method variant requires no difference in the apparatus nor controlling software. FIGS. 4A and 4B summarize the experimental variants for performing this method variant.

Force-Feedback Optical Trapping Subsystem

Figure 5A:
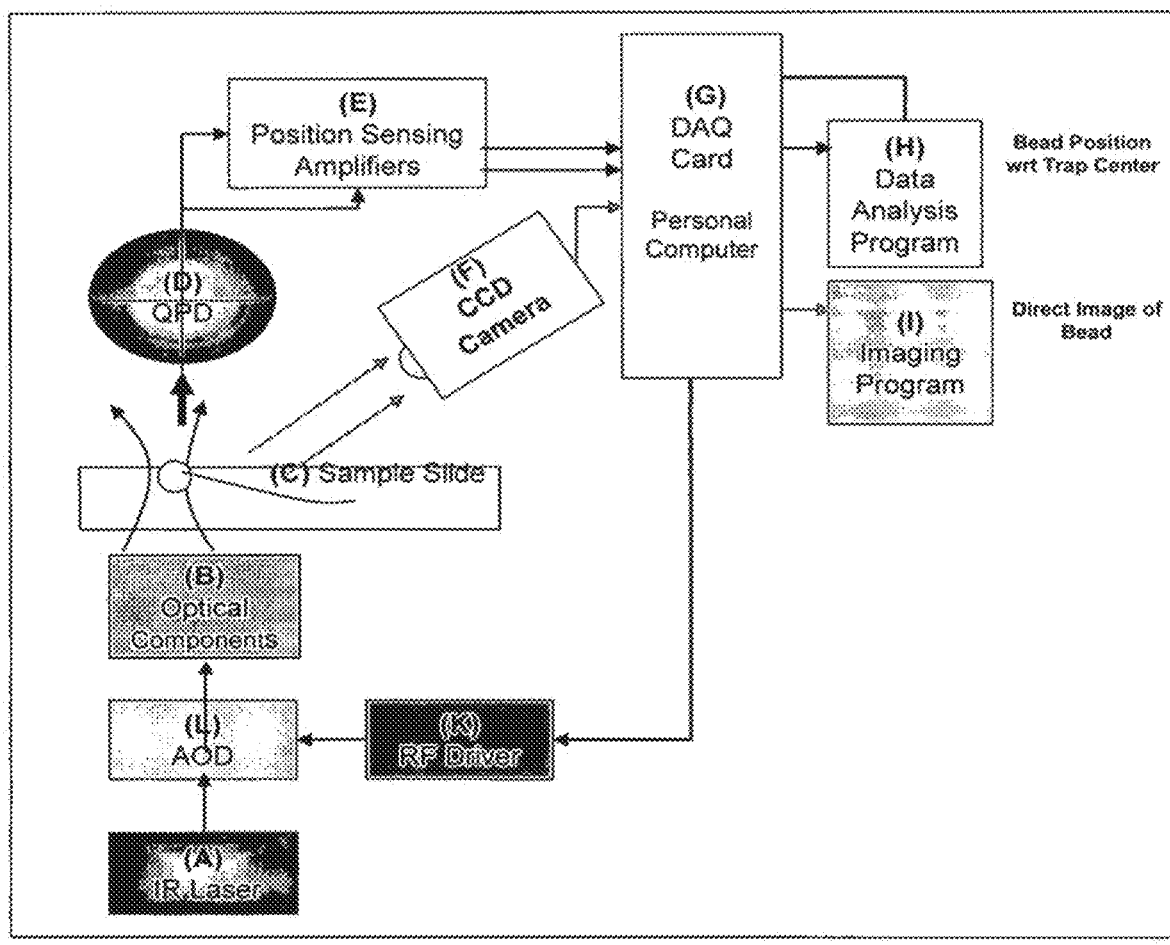
FIG. 5A illustrates schematically the single molecule detection system which includes a representative optical tweezers apparatus that comprises trapping, force detection, beam steering and isotension capabilities and force-feedback optical trapping subsystem that maintains a constant force on a trapped bead, even as the bead experiences other forces due to the enzymatic activity of a polymerase.

FIG. 5A illustrates an exemplary design of an optical trapping system that maintains a constant force on a trapped bead, even as the bead experiences other forces due to the enzymatic activity of the polymerase. An IR laser source (A) is focused via a series of lenses and mirrors (B) to a position (xo, yo) in the sample plane. This focus position, (xo, yo), is established by the deflection angle of a two-axis acousto-optic deflector (AOD) (L). The Gaussian beam profile at the sample slide (C) traps the bead that is attached to either a polymerase (not shown) or nucleic acid template (shown).

A quadrant photodiode or QPD, (D) detects the interference pattern of the IR signal scattering off the bead, and outputs the x and y perturbations of this signal. These signals are amplified (E), obtained by a data acquisition card (DAQ), interfaced to a personal computer (G). This data is subsequently processed in a data acquisition and analysis program (programmed, for example, in Labview® from National Instruments), to determine the position of the bead relative to the center of the optical trap, with near-nanometer resolution and to measure the trapping force on the bead in picoNewtons. (See also FIG. 5B)

Direct images of the bead are captured by a sensitive CCD camera (e.g., Cooke's PixelFly) that is coupled to the light microscope (F). Custom data analysis computer programs provide nm scale position detection of the bead; an image analysis program provides an image of the sample plane, including the trapped bead.

With the force feedback system operating (L, K), the force exerted by the laser on the bead remains constant even in the presence of the enzymatic forces that act on the bead, shifting its position within the trap. This is accomplished via a software program that determines the instantaneous position of the bead with respect to the center of the laser trap and compares this to a reference position (corresponding to a given force on the trapped bead). The difference between this current position and the desired bead position is converted into a two channel frequency signal ($\Delta fx$, $\Delta fy$) that the radio frequency (RF) driver (K) inputs into the two-axis AOD crystal. This radio frequency creates a standing wave in the crystal which then diffracts the incident laser beam. The position of the first order diffracted beam changes with the radio frequency.

Thus the laser beam can be precisely and rapidly steered by controlling the RF input into the AOD crystal. The data acquisition program calculates the new feedback frequency that should be generated by the RF driver (K) to deflect the beam enough to compensate for enzymatically-driven shift in the bead's position. A record of this output frequency can be post-processed to output the time evolution of the trap's position over the polymerization time.

The unique features of NANO-VALID™ drug validation process as compared to conventional approaches are that the NANO-VALID™ system enables high resolution real time tracking of how the drug candidate modifies or interferes the polymerase movement along the nucleic acid template. This system is furthermore, highly integrated and automated making it easily scalable for high throughput drug screening applications.

Figure 8:
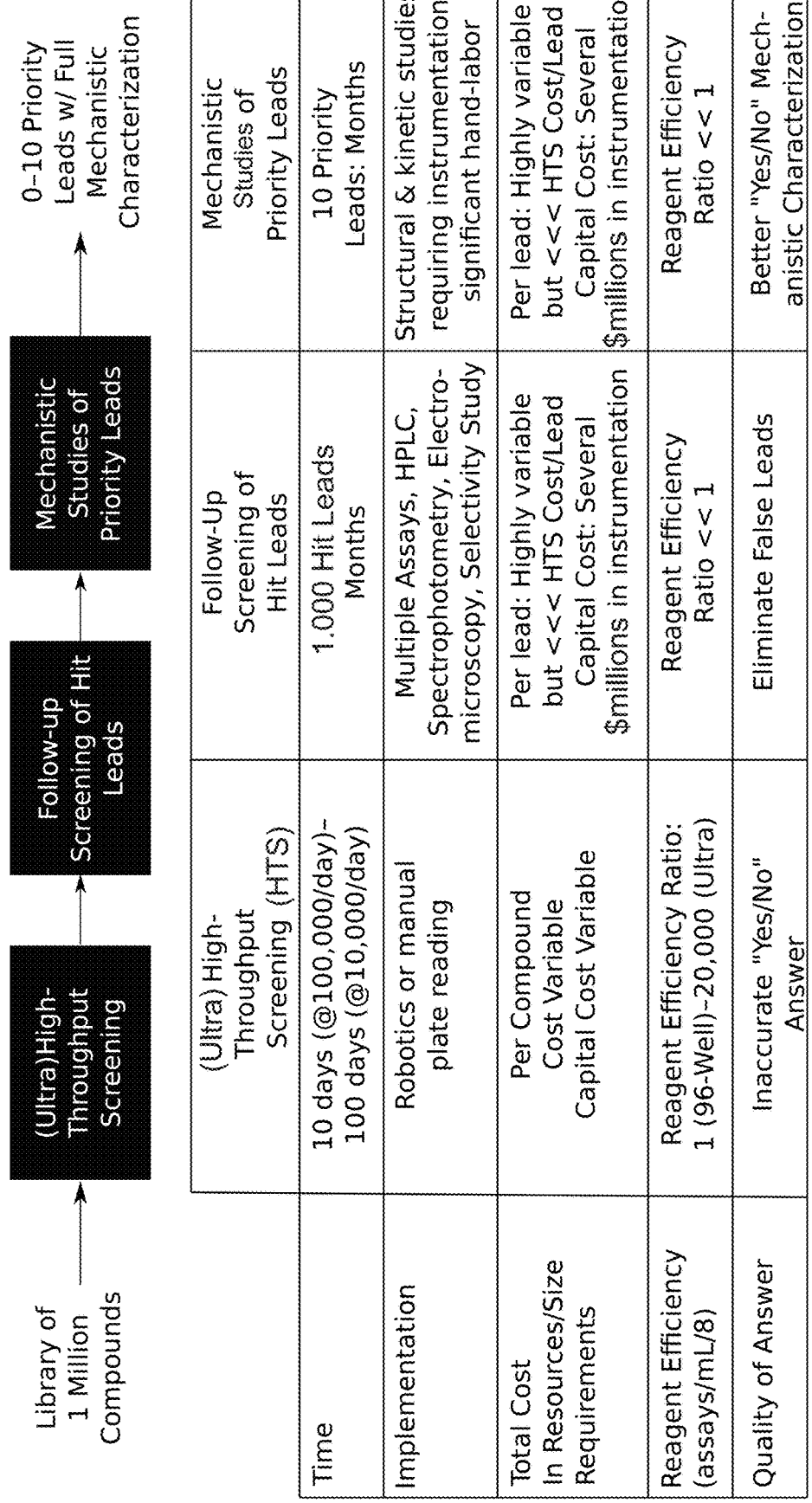
FIG. 8 illustrates key features of the conventional approach to drug screening and discovery.

The methods and apparatuses described herein also provide numerous cost-related advantages over conventional drug screening and validation techniques. As illustrated in FIGS. 8-10, the present methods and apparatus enable rapid screening, providing for an approximately 115-fold reduction in labor time. In addition, the single-molecule approach of the present invention allows for an approximately 130-fold reduction in reagent volumes, and the reduced instrumentation cycle time leads to an approximately 10- to 50-fold reduction in machine time. Thus, overall, the present invention provides an approximately 20- to 100-fold improvement in overall cost.

EXAMPLES

Figure 5B:
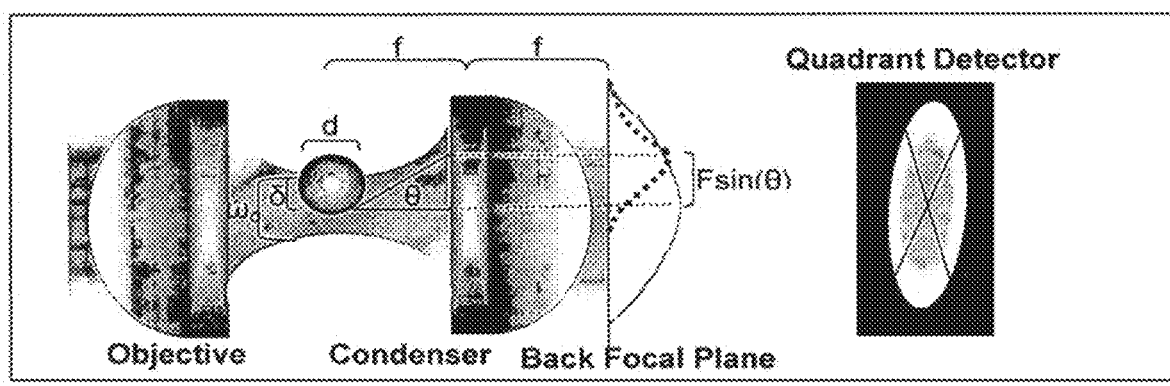
FIG. 5B illustrates the detection system in the single molecule tracking system by which a quadrant photodiode is utilized to detect the displacement of a dielectric sphere from an optical trap's center. The position of the bead with respect to the optical trap is recorded onto this quadrant photodetector. Deviations from this center of the optical well are used to quantify the picoNewton sized forces acting on the bead.

Method and Apparatus for Detecting Inhibition of DNA Replication using Dynamics of Template Length In this example, we illustrate a method and apparatus for detecting the inhibition of DNA replication via single-molecule measurement of the DNA template length. In this example, we seek to screen for drugs that inhibit DNA polymerization through one of two mechanisms: interference of polymerase binding, or ultra-low processivity. FIG. 2A shows an expected normal signature, while FIG. 2B shows a result expected from an effective drug candidate. The apparatus used for single-molecule measurements comprises a force-feedback optical trapping subsystem, as previously described. The experimental setup for this mechanical signature measurement is shown in FIGS. 5A and 5B.

The interior surface of an optically transparent multi-well microplate is coated with streptavidin according to standard methods. A sample of biotinylated ssDNA template with a length exceeding 5 kb is prepared and suspended in a buffered solution. A DNA primer is also designed that can initiate polymerization. A suspension of streptavidin coated 0.5-1 micron beads (available from Bang's Laboratories) is prepared and distributed among the wells; subsequently a solution of the ssDNA template is also distributed among the wells. The plate is incubated for approximately 30 minutes for the streptavidin-biotin bonding to occur such that a sufficient population of DNA tethers are formed, which have one end of the nucleic acid attached to the microplate, the other to a streptavidin-coated bead. The drug candidates are distributed among the wells as follows: each well contains at most one candidate; each candidate is added to N wells to provide redundancy. A set of C wells do not have any candidate added so that they may be used as control samples.

The optical tweezers apparatus is initiated and calibrated from the graphical user interface. The microwell plate is loaded into the optical tweezers apparatus, such that its bottom is flush with the focal plane of the optical trap. The GUI is used to set the interrogation time and the trapping force to a desired value from 0-35 pN. The GUI also is used to identify which candidate (if any) is present in each microwell.

Input is provided to the GUI to drive the microwell plate so that the optical tweezers beam is interrogating the first control microwell. Using a joystick and the CCD image of the sample plane, a suitable bead is trapped manually. The force-feedback system is engaged and immediately thereafter, a buffered suspension of DNA primer, dNTP mixture and the target DNA polymerase is added to this single microwell. This could likewise be applied to RNA polymerase and Reverse transcriptase. The force-feedback system is allowed to run to track the position of the trap during the chosen time interval; these results are stored in memory so that they are addressable and identifiable both by the well address and as a control result. This process is repeated for the remainder of the control wells. From the GUI, a program is run to analyze the multiple control samples in order to extract several salient features common to the polymerase target. First, a selection of different low-pass filters, with cutoff frequencies in the range of 100-1000 Hz, are applied to these controls, and the results displayed so that the user may select the filter with a cutoff frequency roe that gives the highest level of signal smoothing while maintaining the integrity of the overall dynamics of the target polymerase.

Once filtered, a numerical differentiation scheme determines the instantaneous velocity at each point. Next, nearest-neighbor averaging of the velocity is determined for different window-sizes, ranging from the entire acquisition window (i.e., t=[0:T]), down to a window corresponding roughly to 100 base-pairs (windows of approximately 1 second length, depending on the velocity of the polymerase).

Input is provided to the GUI to drive the microwell plate so that the optical tweezers beam is interrogating the first non-control microwell. Using a joystick and the CCD image of the sample plane, a suitable bead is trapped manually. The force-feedback system is engaged and immediately thereafter, a buffered suspension of DNA primer, dNTP mixture and the target DNA polymerase is added to this single microwell. The force-feedback system continues to track the position of the trap during the chosen time interval; these results are stored in memory so that they are addressable and identifiable both by the well address, as well as the drug candidate present. This process is repeated for the remainder of the control wells.

All of the obtained results are filtered with a low-pass filter with cutoff frequency roe. With the GUI, the results are numerically differentiated, and nearest-neighbor velocity plots are calculated for the same time-scales as for the controls. Each drug candidate is considered in turn. Substantially non-zero velocity over any time scale, for any one of the N samples would indicate that the drug candidate had not interfered reliably or efficiently with the DNA replication process. For that reason, those candidates showing a substantially non-zero velocity (e.g., 1% of the average velocity of all of the controls) over any time scale, for any of the N samples, are rejected.

Method and Device for Detecting Early Termination of RNA Polymerase Targets using Dynamics of Polymerase Along DNA Strand In this example, we illustrate a method and apparatus for detecting the early termination of RNA transcription by an RNA polymerase. In this example we are screening for drug candidates that induce early termination of RNA polymerization after initiation at a specific site. FIG. 2A shows an expected normal signature, while FIG. 2B shows a result expected from an effective drug candidate. The apparatus used for single-molecule measurements is a dual beam optical tweezers apparatus that comprises both a force-feedback optical trapping subsystem and a higher-power steerable optical trap.

A sample of double stranded (ds) DNA is prepared via standard methods to comprise both a stalled transcription complex comprising a biotin tag, as well as biotin tag on the downstream end of the DNA (Neuman, K. C., et. Al, Cell, 115: 437-447, 2003). The transcription factor tag is subsequently attached to streptavidin-coated 1 micron diameter dielectric bead (e.g., Bang's Laboratories), and the DNA tag is attached to a streptavidin-coated 0.5 micron diameter dielectric bead (e.g., Bang's Laboratories). This forms a sample of DNA "dumbbells," that have a bead "handle" on each end: one attached to the end of the DNA, the other to the RNA polymerase. The drug candidates are distributed among the wells of an optically transparent microwell plate as follows: each well contains at most one candidate; each candidate is added to N wells to provide redundancy. A set of C wells do not have any candidate added so that they may be used as control samples.

The optical tweezers apparatus is initiated and calibrated from the graphical user interface. The microwell plate is loaded into the optical tweezers apparatus, such that its bottom is flush with the focal plane of the optical trap. The GUI is used to set the interrogation time, T, and the trapping force of the force-feedback beam to a desired value from 0-35 pN. The GUI also is used to identify which candidate (if any) is present iri each microwell, so that the microwells may be subsequently addressed by both their position and contents.

Input is provided to the GUI to drive the microwell plate so that the optical tweezers beam is interrogating the first control microwell. Using a joystick and the CCD image of the sample plane, a dumbbell is trapped manually by trapping the larger bead in the force-feedback optical trap, and the smaller bead in the strong secondary trap. The force-feedback system is engaged and immediately thereafter, a buffered suspension of RNA dNTP mixture is added to this single microwell. The force-feedback system continues to track the position of the trap during the chosen time interval; these results are stored in memory so that they are addressable and identifiable both by the well address and as a control result. This process is repeated for the remainder of the control wells. From the GUI, a program is run that analyzes the multiple control samples in order to extract several salient features common to the polymerase target. First, a selection of different low-pass filters, with cutoff frequencies in the range of 100-1000 Hz, are applied to these controls, and the results displayed so that the user may select the filter with a cutoff frequency roe that gives the highest level of signal smoothing while maintaining the integrity of the overall dynamics of the target polymerase.

Once filtered, a numerical differentiation scheme determines the instantaneous velocity at each point. Next, nearest-neighbor averaging of the velocity is determined for different window-sizes, ranging from the entire acquisition window (i.e., t=[0:T]), down to a window corresponding roughly to 100 base-pairs (windows of approximately 1 second length, depending on the average velocity of the polymerase). The user then selects a timepoint, To<T, via the GUI, that corresponds to the maximum time at which polymerization should still occur (i.e., the time beyond which polymerization should be terminated by an effective drug candidate).

Input is provided to the GUI to drive the microwell plate so that the optical tweezers beam is interrogating the first non-control microwell. Using a joystick and the CCD image of the sample plane, a suitable bead is trapped manually. The force-feedback system is engaged and immediately thereafter, a buffered suspension of RNA dNTP mixture is added to this single microwell. The force-feedback system is allowed to run to track the position of the trap during the chosen time interval; these results are stored in memory so that they are addressable and identifiable both by the well address, as well as the drug candidate present. This process is repeated for the remainder of the control wells.

All of the obtained results are filtered with a low-pass filter with cutoff frequency roe. With the GUI, the results are numerically differentiated, and nearest-neighbor velocity plots are calculated for the same time-scales as the controls. Each drug candidate is considered in turn. If a drug candidate is reliably interfering with transcription in the manner desired, all of the related N samples should show substantially non-zero velocity after the time To. For that reason, those candidates showing a substantially non-zero velocity for any of the N samples (e.g., 1% of the average velocity of all of the controls) for any time window after To are rejected.

While the invention has been described in detail with reference to particular embodiments thereof, it will be apparent to one skilled in the art that various changes can be made, and equivalents employed, without departing from the scope of the invention.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

All publications cited herein are hereby incorporated by reference in their entirety.

The invention claimed is:

1. A system for drug discovery, drug development, drug screening, or drug validation, the system comprising:
   a sample chamber configured to contain a target protein,
      a nucleic acid that interacts with the target protein, and
      a drug candidate that may interfere with the target protein;
   a measurement mechanism configured to manipulate the nucleic acid; and
   a computing device comprising software instructions that, when executed by the computing device, cause the computing device to:
      control the measurement mechanism to maintain a constant tension on the nucleic acid during interaction of the nucleic acid with the target protein;
      measure, via the measurement mechanism, a time-dependent signal representing an interaction between the nucleic acid and the target protein; and
      compare the measured time-dependent signal to a baseline signal for the interaction between the nucleic acid and the target protein to determine whether the interaction is modified by the drug candidate.

2. The system of claim 1, wherein the computing device comprises software instructions that, when executed by the computing device, cause the computing device to determine whether the drug candidate blocks the interaction between the target protein and the nucleic acid.

3. The system of claim 1, wherein the computing device comprises software instructions that, when executed by the computing device, cause the computing device to determine a mechanism of the interaction between the target protein and the drug candidate based on the measured time-dependent signal.

4. The system of claim 1, wherein the measurement mechanism comprises one or more surfaces configured to bind the nucleic acid.

5. The system of claim 1, wherein the measurement mechanism comprises one or more beads configured to bind the nucleic acid.

6. The system of claim 1, wherein the measurement mechanism comprises an optical trap configured to exert a force on the nucleic acid to maintain the constant tension.

7. The system of claim 1, wherein the measurement mechanism comprises a magnetic trap configured to exert a force on the nucleic acid to maintain the constant tension.

8. The system of claim 1, wherein the time-dependent signal comprises a mechanical signature of the interaction of the nucleic acid with the target protein.

9. The system of claim 8, wherein the mechanical signature comprises a change in an elasticity of the nucleic acid.

10. The system of claim 8, wherein the mechanical signature comprises a velocity of the target protein relative to the nucleic acid.

11. The system of claim 8, wherein the mechanical signature comprises a deformation of the nucleic acid.

12. The system of claim 1, comprising the target protein.

13. The system of claim 12, wherein the target protein is an enzyme.

14. The system of claim 13, wherein the enzyme is a nucleic acid polymerase.

15. The system of claim 1, wherein the measurement mechanism is configured to immobilize a first end of the nucleic acid and exert a force on a second end of the nucleic acid to maintain the constant tension on the nucleic acid.

16. The system of claim 1, wherein the computing device comprises software instructions that, when executed by the computing device, cause the computing device to advance or eliminate the drug candidate in a drug trial based on the determination of whether the interaction is modified by the drug candidate.

17. The system of claim 1, wherein the computing device comprises software instructions that, when executed by the computing device, cause the computing device to:
   determine a mechanism of interference of the drug candidate with the interaction between the nucleic acid and the target protein; and
   advance or eliminate the drug candidate in a drug trial based on the mechanism of interference.

18. The system of claim 1, further comprising a microwell plate, wherein:
   the sample chamber is a microwell positioned on the microwell plate;
   the microwell plate comprises a plurality of additional microwells, each configured to contain a target protein, a nucleic acid that interacts with the target protein, and a drug candidate that may interfere with the target protein;
   the measurement mechanism is configured to manipulate the nucleic acid in each of the plurality of additional microwells; and
   the computing device comprises software instructions that, when executed by the computing device, cause the computing device to:
      control the measurement mechanism to maintain a constant tension on the nucleic acid in each of the plurality of additional microwells during interaction of the nucleic acid in each of the plurality of additional microwells with the target protein in each of the plurality of additional microwells;
      measure, via the measurement mechanism, a time-dependent signal for each of the plurality of additional microwells representing an interaction between the nucleic acid and the target protein in each of the plurality of additional microwells; and
      compare each microwell's measured time-dependent signal to a baseline signal for the interaction of the microwell's nucleic acid and target protein to determine whether the interaction in each microwell is modified by the drug candidate.

19. The system of claim 18, wherein the computing device comprises software instructions that, when executed by the computing device, cause the computing device to advance or eliminate the drug candidate of each microwell in a drug trial.

20. The system of claim 19, wherein the nucleic acid and target protein in at least some of the microwells is the same.

* * * * *